United States Patent
Yeo et al.

(10) Patent No.: US 12,421,433 B2
(45) Date of Patent: Sep. 23, 2025

(54) METHOD OF MANUFACTURING SELF-ADHESIVE POLYURETHANE SUBSTRATES VIA SELECTIVE PHOTO-POLYMERIZATION

(71) Applicant: KYUNGPOOK NATIONAL UNIVERSITY INDUSTRY-ACADEMIC COOPERATION FOUNDATION, Daegu (KR)

(72) Inventors: Junyeob Yeo, Daegu (KR); Taeseung Hwang, Daegu (KR); Hee Jin Lee, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 161 days.

(21) Appl. No.: 18/232,775

(22) Filed: Aug. 10, 2023

(65) Prior Publication Data
US 2024/0052218 A1   Feb. 15, 2024

(30) Foreign Application Priority Data
Aug. 10, 2022   (KR) ................. 10-2022-0099764

(51) Int. Cl.
*C09J 175/00*   (2006.01)
*A61B 5/00*   (2006.01)
(Continued)

(52) U.S. Cl.
CPC .......... *C09J 175/00* (2013.01); *A61B 5/6832* (2013.01); *A61F 7/007* (2013.01); *C09J 9/02* (2013.01);
(Continued)

(58) Field of Classification Search
CPC ... A61B 5/6832; A61F 7/007; C09J 2301/416
See application file for complete search history.

(56) References Cited

U.S. PATENT DOCUMENTS

| 2012/0172477 A1* | 7/2012 | Huang | .................. C09J 133/14 522/79 |
| 2022/0061714 A1* | 3/2022 | Park | ..................... A61B 5/6824 |

FOREIGN PATENT DOCUMENTS

| JP | 05-125557 A | 5/1993 |
| KR | 10-2002-0056022 A | 7/2002 |

(Continued)

OTHER PUBLICATIONS

Huang, Xian et al., "Materials and designs for wireless epidermal sensors of hydration and strain" (First published Mar. 2, 2014), Advanced Functional Materials, vol. 24, pp. 3846-3854, Wiley-VCH Verlag GmbH & Co. (Jul. 2, 2014).

*Primary Examiner* — Daniel McNally
(74) *Attorney, Agent, or Firm* — Bridgeway IP Law Group, PLLC; Sang Ho Lee; Hyun Woo Shin

(57) ABSTRACT

Provided is a method of manufacturing self-adhesive polyurethanes using selective photo-polymerization. The method of manufacturing self-adhesive polyurethanes using photo-polymerization relates to a method for manufacturing photo-polymerized self-adhesive polyurethane substrates applicable to biocompatible epidermal soft sensors and attachable epidermal thermal heaters without particularly adding an adhesive additive.

13 Claims, 38 Drawing Sheets
(38 of 38 Drawing Sheet(s) Filed in Color)

(51) Int. Cl.
*A61F 7/00* (2006.01)
*C09J 9/02* (2006.01)
*C09J 11/04* (2006.01)
*C09J 11/06* (2006.01)

(52) U.S. Cl.
CPC ................ *C09J 11/04* (2013.01); *C09J 11/06* (2013.01); *A61F 2007/0052* (2013.01); *C09J 2301/416* (2020.08); *C09J 2301/50* (2020.08)

(56) References Cited

FOREIGN PATENT DOCUMENTS

| | | |
|---|---|---|
| KR | 10-0403667 B1 | 4/2004 |
| KR | 10-1006182 B1 | 1/2011 |
| KR | 10-2012-0078638 A | 7/2012 |
| KR | 10-1449745 B1 | 10/2014 |
| KR | 10-2019-0023545 A | 3/2019 |
| KR | 10-2286444 B1 * | 7/2021 |
| KR | 10-2022-0085232 A | 6/2022 |

* cited by examiner

METHOD OF MANUFACTURING SELF-ADHESIVE POLYURETHANE SUBSTRATES VIA SELECTIVE PHOTO-POLYMERIZATION

CROSS-REFERENCE TO RELATED APPLICATION

This application claims priority to and the benefit of Korean Patent Application 10-2022-0099764 filed on Aug. 10, 2022, the disclosure of which is incorporated herein by reference in its entirety.

BACKGROUND

1. Field of the Invention

The present description relates to a method of manufacturing self-adhesive polyurethane (SAPU) substrates using selective photo-polymerization, and specifically, a method of manufacturing photo-polymerized SAPU substrates applicable to biocompatible epidermal soft sensors and attachable epidermal thermal heaters without particularly adding an adhesive additive.

2. Discussion of Related Art

The epidermal electronic system (EES) is emerging as a wearable platform in the Internet of Things in the era of the Fourth Industrial Revolution. The epidermal electronic system can provide real-time physiological signal and motion monitoring through multifunctional sensors as well as thermal therapy and healthcare through thermal heaters, thereby increasing user convenience. Because the epidermal electronic system directly interacts with the human skin, it is important not to induce conformal contact and skin reactions. In particular, to obtain accurate physiological and physical signals on a curved surface, dynamic motion such as that of human skin and organs and conformal contact of the skin are considered to be very important in the epidermal electronic system. However, due to a lack of adhesive force, most of the previous studies indirectly applied an epidermal electronic system to human skin by using auxiliary gloves, and toxic adhesive tape was used in some epidermal electronic systems. Various approaches that are currently implemented for the use of an epidermal electronic system are primarily focused on conformal contact through strong adhesion and biocompatibility between the skin and soft backbone substrate while reducing pain and skin trauma.

Since the polymer materials used as a soft backbone substrate do not exhibit adhesive properties, additional additives, such as organic additives, must be added to an epidermal electronic system to provide adhesive properties. In addition, in view of the biocompatibility of an epidermal electronic system, research is being conducted extensively to apply elastomeric polymers as a soft backbone substrate. Therefore, considerable research has been conducted on epidermal electronic systems that can achieve stable sensing performance in a harsh environment while maintaining conformal contact with the epidermis by optimizing the synthesis ratio between organic additives and elastomers. Among the various available elastomers, polyurethane (PU) has been investigated as a soft backbone substrate for epidermal electronic systems because of its excellent mechanical properties and biocompatibility. In addition, since liquid polyurethane can be easily mixed with various conductive materials such as carbon-based materials, ionic liquids, metal films, and metal nanowires, functionalized polyurethane exhibits improved performance in various stretchable devices, including various multifunctional sensors and epidermal electronic systems.

However, like other elastomers, most polyurethane-based stretchable electronics have the problem that conformal contact with human skin is insufficient due to their lack of adhesive properties. Despite their high stretchability and biocompatibility compared to hydrogel-based materials and self-adhesive elastomers, which have been actively studied for many years, polyurethane-based devices exhibit imperfect conformal contact, which is essential for epidermal electronic systems. Therefore, studies have been conducted by employing various approaches, including the methods described above, such as a method of further adding an adhesive additive to form adhesive properties of polyurethane, a method of modifying the surface, and a method of forming a crosslinking network. A recent study on polyurethane-based epidermal electronic systems showed improved adhesion performance without peeling caused by poor adhesion. Nevertheless, adding an adhesive layer to polyurethane still has limitations. For example, multiple molds and complex procedures are required to fabricate complex nanostructures to impart adhesive properties. In addition, the choice of organic materials to modify the hydrogen bond interactions and crosslinking networks to form adhesive properties in polyurethanes is still limited. Consequently, to maintain the advantageous intrinsic properties of polyurethane for efficient conformal contact, an easy method for imparting stable adhesive properties to polyurethane is required.

The present description provides a method of forming self-adhesive polyurethane substrates using laser-driven selective photo-polymerization without a further additive and manufacturing epidermal soft devices (e.g., sensor and attachable thermal heaters) based on the photo-polymerized self-adhesive polyurethane substrates.

Various laser parameters (e.g., laser power, laser scanning speed, and laser scanning spacing distance) are adjusted to modify the crosslinked network of polyurethane during photo-polymerization so that the various mechanical/chemical properties of polyurethane can be exhibited. The crosslinked network of polyurethane can be modified during photo-polymerization under specific laser scanning conditions to improve the softness and adhesive properties of polyurethane. In addition, a biocompatibility test confirmed that the polymerized polyurethane remained harmless to the skin. Finally, a self-adhesive polyurethane-based epidermal soft sensor and a thermal heater were fabricated by using a silver nanowire (Ag NW) network as a conductive electrode. Such a device can detect human motion and human vital signs and can be used for devices that can interact with human skin, such as in skin thermal therapy.

SUMMARY OF THE INVENTION

The purpose of the present description is to provide a method of manufacturing photo-polymerized self-adhesive polyurethane substrates that can be applied to a biocompatible epidermal soft sensor and an attachable epidermal thermal heater without adding any particular adhesive additive.

To achieve the purpose described above, the present description discloses the following means.

In one aspect, the present description discloses a method of manufacturing a self-adhesive polyurethane using selective photo-polymerization, the method comprising: manufacturing a mixed resin in which a urethane acrylate oligomer and a photoinitiator are mixed; depositing the mixed resin to manufacture a polyurethane substrate; and performing selective photo-polymerization of the deposited polyurethane substrate with a laser device to manufacture a self-adhesive polyurethane substrate.

In another aspect, the present description discloses a method of manufacturing epidermal soft sensors, the method comprising: manufacturing a mixed resin in which a urethane acrylate oligomer and a photoinitiator are mixed; depositing the mixed resin to manufacture a polyurethane substrate; performing selective photo-polymerization of the deposited polyurethane substrate with a laser device to manufacture a self-adhesive polyurethane substrate; and spraying silver nanowires on the self-adhesive polyurethane substrate to form a nanowire network.

In a final aspect, the present description discloses a method of manufacturing attachable epidermal thermal heaters, the method comprising: coating an organic conductor on a glass substrate; depositing silver nanowires on the glass conductor; patterning the deposited silver nanowires; and attaching a photo-polymerized self-adhesive polyurethane substrate on the patterned silver nanowires.

The manufacturing method, according to the present description, has the advantage of being able to manufacture self-adhesive polyurethane substrates having high adhesion and low Young's modulus comparable to human skin by adjusting photo-polymerization conditions (various laser parameters).

There is an advantage of being able to be further applied to wearable devices such as a biocompatible epidermal soft sensor based on the photo-polymerized self-adhesive polyurethane substrate manufactured according to the present description and an attachable epidermal thermal heater having a silver nanowire network.

In addition, there is an advantage that the epidermal soft sensor based on the photo-polymerized self-adhesive polyurethane substrate can successfully detect human motion and vital signs, and that the attachable epidermal thermal heater can efficiently transfer heat to the epidermis due to its excellent conformal contact properties to human skin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10A shows electrical characteristics under the various applied strains; FIG. 10B shows the results of cyclic tests under various strains controlled by a linear stage; FIG. 10C shows the results of tests repeated at various index finger angles (20°, 40°, 60°, 80°, 90°) in the state where an epidermal soft sensor (Fabrication Example 1) based on the photo-polymerized self-adhesive polyurethane substrate (Example 1) was attached; FIG. 10D shows the sensing characteristics according to cyclic tests at various speeds; FIG. 10E shows the resistance measurement results of multiple motion detection at the index and middle fingers; FIG. 10F shows the degree to which signals were maintained while keeping the wrist at various angles; FIG. 10G shows the heart rate measurement results when an epidermal soft sensor (Fabrication Example 1) based on the photo-polymerized self-adhesive polyurethane substrate (Example 1) was attached to the chest; FIG. 10H shows the heart rate measurement results measured when an epidermal soft sensor (Production Example 1) based on the photo-polymerized self-adhesive polyurethane substrate (Example 1) was attached to the carotid artery; and FIG. 10I shows the heart pulse signals (blue dotted line box) measured during the cardiac cycle.

FIG. 12A shows the temperature distribution and change depending on different applied voltages; FIG. 12B shows an attachable thermal heater applied to various materials; FIG. 12C shows the heat transfer to the epidermis indicated by the X pattern of the non-adhesive thermal heater/the self-adhesive thermal heater after detachment; FIG. 12D shows the results of the computational simulation of the heat transfer of the non-adhesive thermal heater/the self-adhesive thermal heater; and FIG. 12E shows the change of the temperature and electrical conductivity of the attachable epidermal thermal heater depending on the motion of the index finger.

DETAILED DESCRIPTION OF THE EMBODIMENTS

Figure 1:
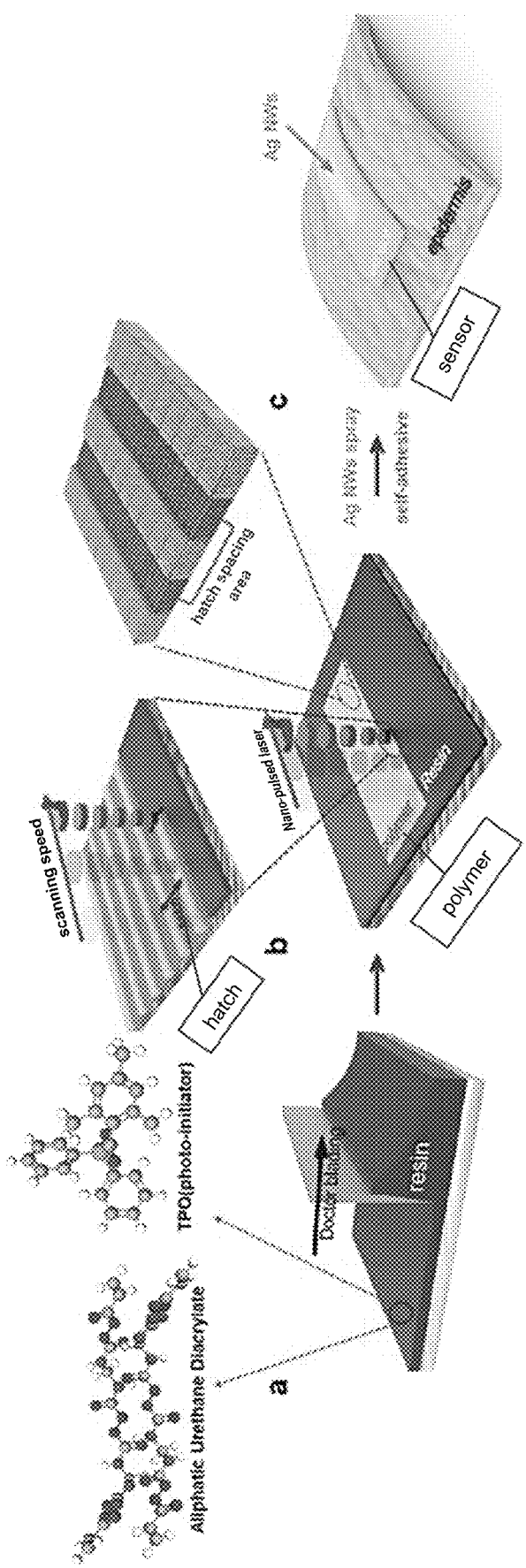
FIG. 1 is a schematic diagram of a method of manufacturing a self-adhesive polyurethane-based self-adhesive epidermal soft device, comprising: a) depositing a mixed resin of aliphatic urethane diacrylate and diphenyl (2,4,6-trimethylbenzoyl)phosphine oxide (TPO) on a stage by using a doctor blading technique; b) manufacturing a photo-polymerized polyurethane substrate based on a selective photo-polymerization process; and c) depositing silver nanowires (Ag NWs) on the surface of a self-adhesive polyurethane and attaching to the epidermis.

Hereinafter, the present description will be described in more details.

The detailed description is as follows. The terms used in the present Specification have been selected as much as possible from general terms that are widely used at present, while considering the functions in the present description. However, they may vary depending on the intention of one of ordinary skill in the art or a precedent, the emergence of new technologies, and the like. In addition, in specific cases, there are also terms arbitrarily selected by the applicant, and in these cases, the meaning will be described in detail in the corresponding detailed description of the invention. Therefore, the terms used in the present description should be defined based on the meaning of the terms and the overall content of the present description, not simply the names of the terms.

Unless defined otherwise, all terms used herein, including technical or scientific terms, have the same meaning as commonly understood by one of ordinary skill in the art to which the present description belongs. Terms such as those defined in commonly used dictionaries should be interpreted as having a meaning consistent with the meaning in the context of the related art, and are not interpreted in an ideal or excessively formal sense unless explicitly defined in the present application.

Numerical ranges are inclusive of the values defined therein. Every maximum numerical limitation given throughout the present Specification includes every lower numerical limitation, as if such lower numerical limitations were expressly written. Every minimum numerical limitation given throughout the present Specification includes every higher numerical limitation, as if such higher numerical limitations were expressly written. Every numerical limitation given throughout the present Specification will include every better numerical range within the broader numerical range, as if the narrower numerical limitations were expressly written.

Hereinafter, each description and embodiment disclosed in the present description can also be applied to other descriptions and embodiments for each. Therefore, all combinations of the various elements disclosed herein fall within the scope of the present description. In addition, the scope of the present description is considered as being limited by the specific descriptions described below.

Expressions such as "comprising" used in the present Specification should be understood as open-ended terms that include the possibility of including other embodiments, unless specifically stated otherwise in a phrase or sentence in which the expression is included.

Since the advent of the Fourth Industrial Revolution, as research and development of wearable devices have continued, interest in elastomers that can be modified to fit the body has also increased. Among them, polyurethane has been widely used due to its excellent mechanical properties and biocompatibility. However, in many research processes, polyurethane showed a lack of adhesive force, which naturally meant a limitation as a wearable device. Therefore, the inventors of the present description propose a method of manufacturing a self-adhesive polyurethane using laser as a method for solving this problem.

Specifically, the inventors of the present description have completed the present description by confirming that polyurethane manufactured by using optimized UV pulse laser conditions can exhibit sufficiently high elasticity in consideration of the degree of maximum elongation of human skin and that it can also exhibit high adhesive strength so that it can be used as a wearable device such as a motion sensor that requires tight adhesion to the skin and a wearable heater that can be used by being attached to the human body based on heat conduction.

Hereinafter, the present description is described in detail.

Manufacturing Method of Self-Adhesive Polyurethane Using Selective Photo-Polymerization The present description discloses a method of manufacturing a self-adhesive polyurethane using selective photo-polymerization described below.

Specifically, the present description relates to a method of manufacturing a self-adhesive polyurethane using selective photo-polymerization, the method comprising: manufacturing a mixed resin in which a urethane acrylate oligomer and a photoinitiator are mixed; depositing the mixed resin to manufacture a polyurethane substrate; and performing selective photo-polymerization of the deposited polyurethane substrate with a laser device to manufacture a self-adhesive polyurethane substrate.

In the present description, the urethane acrylate oligomer may be at least one selected from the group consisting of aliphatic urethane diacrylate, aliphatic urethane hexaacrylate, aliphatic urethane triacrylate, aromatic urethane diacrylate, aromatic urethane triacrylate, and aromatic urethane hexaacrylate, and specifically, it may be an aliphatic urethane acrylate-based oligomer, preferably an aliphatic urethane diacrylate, and it is not limited thereto.

In the present description, the photoinitiator may be at least one selected from the group consisting of camphorquinone, 2-(dimethylamino methacrylates), phenylbis(2,4,6-trimethylbenzoyl)phosphine oxide, and diphenyl(2,4,6-trimethylbenzoyl)phosphine oxide, and preferably, it may be diphenyl(2,4,6-trimethylbenzoyl)phosphine oxide, but is not limited thereto.

In the present description, the mixed resin may be a mixture of a urethane acrylate oligomer and a photoinitiator in a weight ratio of 15 to 35:1, and specifically, it may be a mixture in a weight ratio of 18 to 30:1, but is not limited thereto.

In the present description, the polyurethane substrate may have an average thickness of 150 to 350 μm, and specifically, it may have an average thickness of 180 to 300 μm, but is not limited thereto.

In the present description, the selective photo-polymerization may be selectively photo-polymerizing a polyurethane substrate by adjusting a laser scanning speed and a laser scanning spacing distance of a laser device, but is not limited thereto.

In the present description, the laser scanning speed may be 250 to 350 mm/s, specifically 280 to 320 mm/s, preferably 300 mm/s, but is not limited thereto.

In the present description, the laser scanning spacing distance may be 0.5 to 12 μm, specifically, 1 to 10 μm, but is not limited thereto.

As will be described later in the present description, the polyurethane substrate is selectively polymerized to have self-adhesiveness by adjusting the laser scanning speed and the laser scanning spacing distance among the parameters of a laser device.

At this time, when the laser scanning spacing distance is 1 μm while the laser scanning speed exceeds 350 mm/s, a polyurethane substrate is easily torn, and when the laser scanning distance is 15 μm while the laser scanning speed exceeds 350 mm/s, non-polymerization occurs.

In addition, when the laser scanning spacing distance is 1 μm and the laser scanning speed is less than 250 mm/s, especially at 50 mm/s and 100 mm/s, since high energy density is applied, a rapid decrease of the degree of adhesion occurs.

Therefore, to manufacture a polyurethane substrate with self-adhesive properties through the selective photo-polymerization according to the present description, it is necessary to optimally combine the laser scanning speed and the laser scanning spacing distance among various laser device parameters, and when the laser scanning speed is 250 to 350 mm/s and the laser scanning spacing distance is 1 to 10 μm, problems that have not been solved conventionally can be solved, and most preferably, when the laser scanning speed is 300 mm/s, and the laser scanning spacing distance is 10 μm, optimal characteristics can be given.

By performing selective photo-polymerization at the optimal laser scanning speed and laser scanning spacing distance described above, self-adhesive polyurethane substrates having high adhesive force and low Young's modulus comparable to human skin can be manufactured.

Method of Manufacturing Epidermal Soft Sensors

The present description discloses a method of manufacturing epidermal soft sensors as follows.

Specifically, the present description relates to a method of manufacturing epidermal soft sensors, the method comprising: manufacturing a mixed resin in which a urethane acrylate oligomer and a photoinitiator are mixed; depositing the mixed resin to manufacture a polyurethane substrate; performing selective photo-polymerization of the deposited polyurethane substrate with a laser device to manufacture a self-adhesive polyurethane substrate; and spraying silver nanowires on the self-adhesive polyurethane substrate to form a nanowire network.

In the present description, the silver nanowires may have an average length of 100 to 200 μm and an average diameter of 80 to 120 nm, but are not limited thereto.

In the present description, when forming a silver nanowire network by spraying silver nanowires, a silver nanowire solution obtained by mixing silver nanowires in ethanol may be sprayed onto a self-adhesive polyurethane substrate, but the method is not limited thereto.

The contents about the method of manufacturing self-adhesive polyurethane using selective photo-polymerization described above may all be applied to the method of manufacturing epidermal soft sensors unless they contradict with each other.

Method of Manufacturing Attachable Epidermal Thermal Heaters

The present description discloses a method of manufacturing attachable epidermal thermal heaters as follows.

Specifically, the present description relates to a method of manufacturing attachable epidermal thermal heaters, the method comprising: coating an organic conductor on a glass substrate; depositing silver nanowires on the glass conductor; patterning the deposited silver nanowires; and attaching a photo-polymerized self-adhesive polyurethane substrate on the patterned silver nanowires.

In the present description, the organic conductor may be poly(3,4-ethylenedioxythiophene)-poly(styrenesulfonate) (PEDOT:PSS) or polyaniline (PANI), but is not limited thereto.

In the present description, the patterning silver nanowires may be patterning by using a UV laser at 10 mW power, but it is not limited thereto.

In the present description, the photo-polymerized self-adhesive polyurethane substrate is one that is selectively photo-polymerized, has a gap between the photo-polymerized portion and the non-photo-polymerized portion, and may have self-adhesive properties. Specifically, it may be one manufactured by the method of manufacturing a self-adhesive polyurethane using selective photo-polymerization described above.

In the present description, the photo-polymerized self-adhesive polyurethane substrate may have an average thickness of 200 to 400 μm, but is not limited thereto.

In the case of the attachable epidermal thermal heater manufactured by the method of manufacturing attachable epidermal thermal heaters according to the present description, heat conduction and heat transfer can be efficiently performed due to conformal contact, and the heat generated from the silver nanowires can be transmitted to the epidermis. The advantages described above may be considered as possible because the photo-polymerized self-adhesive polyurethane substrate (Example 1), according to the present description, is a material suitable for wearable epidermal devices.

The contents about the method of manufacturing self-adhesive polyurethane using selective photo-polymerization described above may all be applied to the method of manufacturing attachable epidermal thermal heaters unless they contradict with each other.

Hereinafter, the present description will be described in detail based on Examples. However, as long as the following Examples are only for illustrating the present description, the scope of the present description is not limited thereto.

Example: Preparation of Photo-Polymerized Self-Adhesive Polyurethane Substrates

Example 1

A mixed resin was manufactured by mixing 1000 g of aliphatic urethane diacrylate (AUD, EBECRYL 8413, Allnex) and 40 g of diphenyl(2,4,6-trimethylbenzoyl)phosphine oxide (TPO, Sigma Aldrich), which is a photoinitiator.

The manufactured mixed resin of aliphatic urethane diacrylate and diphenyl(2,4,6-trimethylbenzoyl)phosphine oxide was put into a custom-made heat resin bath before printing by using a doctor blading technique, and then heated to 30° C. Thereafter, it was deposited to a thickness of 200 μm by using a 3D linear stage (X-LSQ150B, Zaber).

A polyurethane substrate was manufactured through selective photo-polymerization by using a 3D linear stage, a pulsed ultraviolet laser (Poplar-355-3A, Huaray, 355 nm, 50.1 ns at 200 kHz) and a galvanometer scanner (hurry-SCAN II 10, SCANLAB) with a resin bath after setting the laser scanning speed to 300 mm/s and the laser scanning spacing distance to 10 μm (At this time, the laser power and the laser repetition rates were fixed at 1.4 mW and 200 kHz, respectively, to simplify the experimental conditions.).

Subsequently, the polyurethane substrate was sonicated with a sonicator (POWER SONIC 510, Hwashin Technology) at a frequency of 40 kHz to wash off the residue, immersed in ethanol (ethyl alcohol, 94.5%, SAMCHUN CHEMICALS Co., Ltd) for 3 minutes, and then dried to manufacture a photo-polymerization self-adhesive polyurethane substrate (see FIG. 1).

Example 2

A self-adhesive polyurethane substrate was manufactured under the same conditions as in Example 1, except for setting the laser scanning speed to 300 mm/s and the laser scanning spacing distance to 5 μm.

Example 3

A self-adhesive polyurethane substrate was manufactured under the same conditions as in Example 1, except for setting the laser scanning speed to 300 mm/s and the laser scanning spacing distance to 1 μm.

COMPARATIVE EXAMPLES

Comparative Example 1

A photo-polymerized self-adhesive polyurethane substrate was manufactured under the same conditions as in Example 1, except for adjusting the laser scanning speed to 400 mm/s and the laser scanning spacing distance to 15 μm.

Comparative Example 2

A photo-polymerized self-adhesive polyurethane substrate was manufactured under the same conditions as in Example 1, except for adjusting the laser scanning speed to 400 mm/s and the laser scanning spacing distance to 1 μm.

Comparative Example 3

A self-adhesive polyurethane substrate was manufactured under the same conditions as in Example 1, except for adjusting the laser scanning spacing distance to 15 μm.

Comparative Example 4

A self-adhesive polyurethane substrate was manufactured under the same conditions as in Example 1, except for adjusting the laser scanning speed to 100 mm/s and the laser scanning spacing distance to 10 μm.

Comparative Example 5

A self-adhesive polyurethane substrate was manufactured under the same conditions as in Example 1, except for adjusting the laser scanning speed to 50 mm/s and the laser scanning spacing distance to 10 μm.

EXPERIMENTAL EXAMPLES

Experimental Example 1: Evaluation of Mechanical and Adhesive Properties of Self-Adhesive Polyurethane Substrates 1. Evaluation Method The surface roughness of the self-adhesive polyurethane substrates was observed by using a field emission scanning electron microscope (FE-SEM; SU8220, Hitachi). A strain-stress curve was with a photo-polymerized self-adhesive polyurethane film having a size of 58 mm×20 mm and a thickness of 200 μm by using a universal testing machine (SFM-100 kN, United Calibration). For accurate measurement in the adhesion test, a commercially available adhesive (Magic Tape, 3M) was attached to the self-adhesive polyurethane base samples and detached by using a linear stage (X-LHM150A, Zaber) and a digital force gauge (DST-50N, IMADA). A self-adhesive polyurethane substrate having a size of 58 mm×20 mm and a thickness of 200 μm was peeled off from the skin at a peeling rate of 20 mm/s.

2. Evaluation Results

Since the mixed resin of AUD and TPO can selectively absorb UV energy, the photo-polymerization is considered to depend on the laser scanning path. Therefore, various laser parameters (e.g., laser power, laser scanning speed, and laser scanning spacing distance) that may affect the mechanical and adhesive properties of the photo-polymerized polyurethane substrates were set differently as Examples and Comparative Examples.

Figure 2:
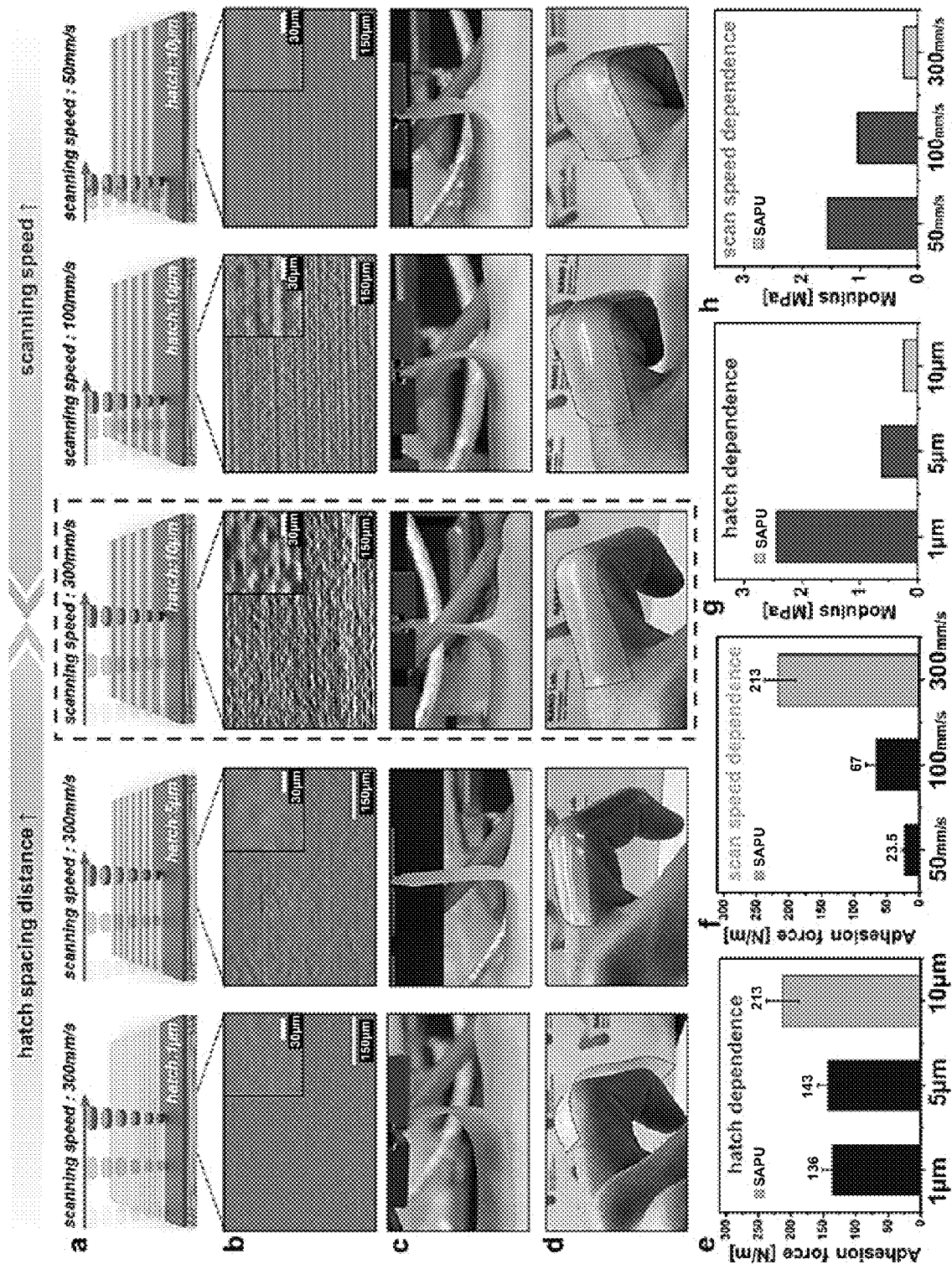
FIG. 2 illustrates the adjustability of mechanical and adhesive properties: (a) is a schematic diagram of laser scanning under various laser scanning speeds and hatch spacing distance conditions; (b) shows field emission scanning electron microscopy images of polyurethane substrates under various laser scanning conditions (laser scanning speed and hatch spacing); (c) and (d) show digital images of the adhesive force measured in the normal direction after attaching to the epidermis (c) and the bent finger (d) the self-adhesive polyurethane substrates according to Examples and Comparative Examples; (e) shows the measured adhesive force of the polyurethane substrates according to the hatch spacing to the epidermis; (f) shows measured adhesive force of the polyurethane substrates according to the laser scanning speed to the epidermis; (g) shows the Young's modulus of the polyurethane substrates according to the hatch spacing; and (h) shows the Young's modulus of the polyurethane substrates according to the laser scanning speed.

FIG. 2 shows the process of imparting adhesive properties to the photo-polymerized self-adhesive polyurethane substrates of Examples and Comparative Examples according to various laser parameters. At this time, the laser power and laser repetition rate were fixed at 1.4 mW and 200 kHz, respectively, to simplify the experimental conditions.

Figure 3:
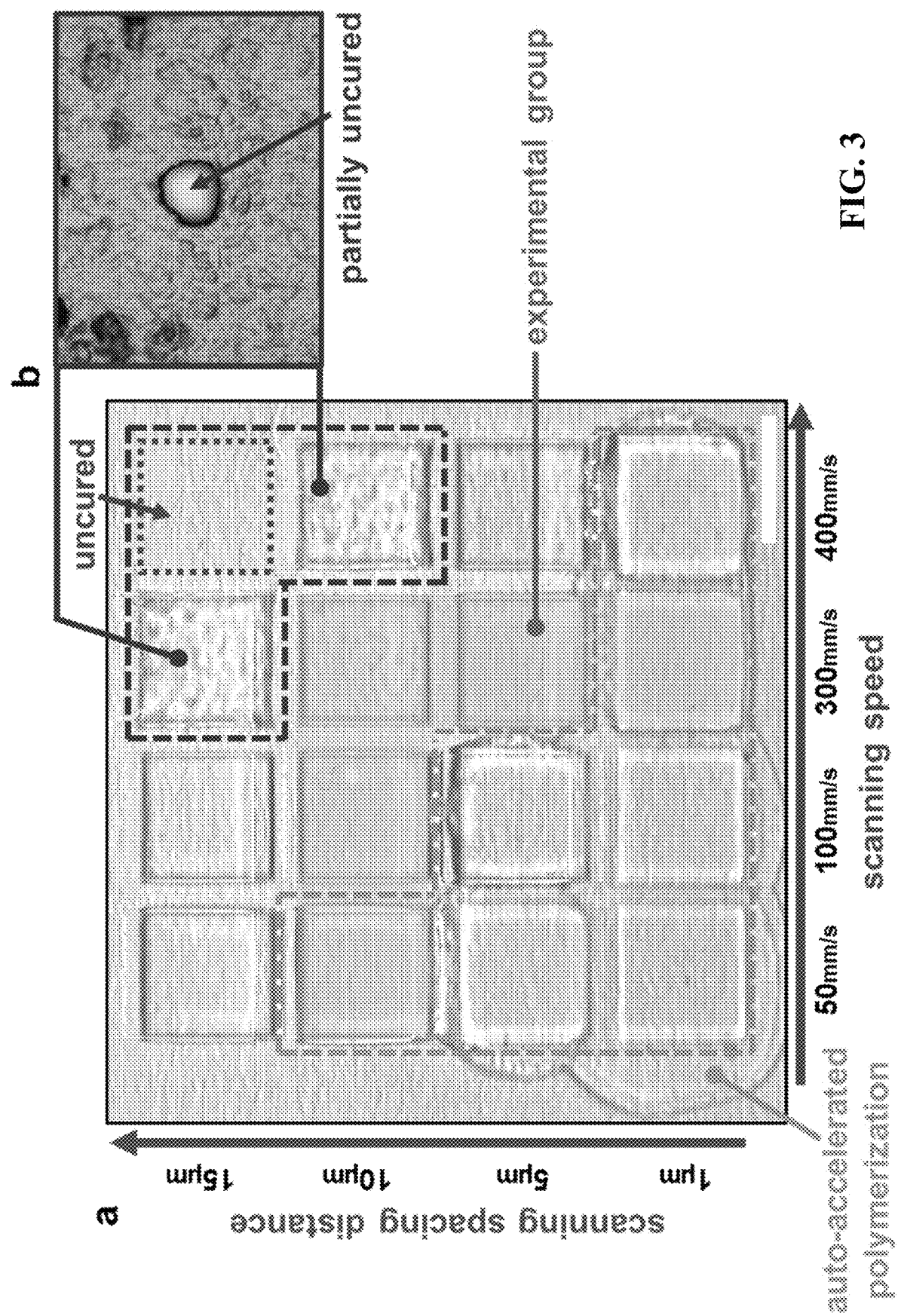
FIG. 3 shows (a) digital images of the photo-polymerized self-adhesive polyurethane according to various laser parameters (e.g., laser power, laser scanning speed, and laser scanning spacing distance) and (b) images of partially uncured polyurethane.

Different laser scanning speeds (i.e., 50 to 400 mm/s) and laser scanning spacing distances (i.e., 1 to 15 µm) were selected to optimize the laser parameters with respect to the adhesive properties of the photo-polymerized polyurethane substrate (FIG. 3). It was confirmed that the photo-polymerized polyurethane substrate could be easily torn and partially cured under extreme conditions of a scanning speed of 400 mm/s (Comparative Example 1) or a scanning spacing distance of 15 µm (Comparative Example 2). Therefore, it was confirmed that the photo-polymerized polyurethane substrate could be stably manufactured at a laser scanning speed of 300 mm/s and a laser scanning spacing distance (1-10 µm) (see (a) of FIG. 2 and FIG. 3).

Since the intensity distribution of the applied laser beam was Gaussian, the focused beam diameter of $1/e^2$ was ~4.8 µm.

Although the diameter of the focused laser beam and the length of the scanning spacing distance were similar, since photo-polymerization occurs above the reaction threshold of the radical density by the laser energy, various trends were found depending on the laser scanning speed (a product of the laser power and the laser residence time).

Therefore, complete photo-polymerization was observed in the SEM image when the scanning spacing distance (1 µm) was smaller than the focused beam diameter (see the left image in (b) of FIG. 2).

However, as the laser scanning spacing distance increased, alternating laser and autocured lines were clearly observed when the focused laser beam diameter (~4.8 µm) was smaller than the laser scanning distance (10 µm) (see the middle image in (b) of FIG. 2).

Similarly, as the applied laser scanning speed increased, alternate laser and autocured lines became clear when the laser scanning spacing distance was fixed at 10 µm (see the right image in (b) of FIG. 2).

After washing the photo-polymerized polyurethane substrate, the photo-polymerized polyurethane substrate was peeled off from the volunteer's back skin in a normal direction, and the correlation between adhesive change and laser parameters (i.e., laser scanning speed and scanning spacing distance) was investigated by measuring the adhesive force.

Through the physical volume of the backhand skin dangled from the self-adhesive polyurethane substrate, an increase of the adhesive force in the normal direction was qualitatively observed as both the laser scanning speed and the scanning spacing distance increased (see (c) of FIG. 2).

(e) and (f) of FIG. 2 show the adhesive force quantitatively measured in the normal direction of the photo-polymerized polyurethane substrate through adhesive force measurement. The measured adhesive force of the self-adhesive polyurethane substrate was similar but slightly different depending on the laser scanning speed and the scanning spacing distance. Specifically, it was confirmed that when the scanning spacing distance was increased, the adhesive force increased by 1.5 times from 136 N/m to 213 N/m, but when the laser scanning speed was increased, the adhesive force was increased by 9 times from 23.5 N/m to 213 N/m. It was confirmed that despite the slight difference, the laser scanning speed and the scanning spacing distance affected the increase of the adhesive force.

Figure 4:
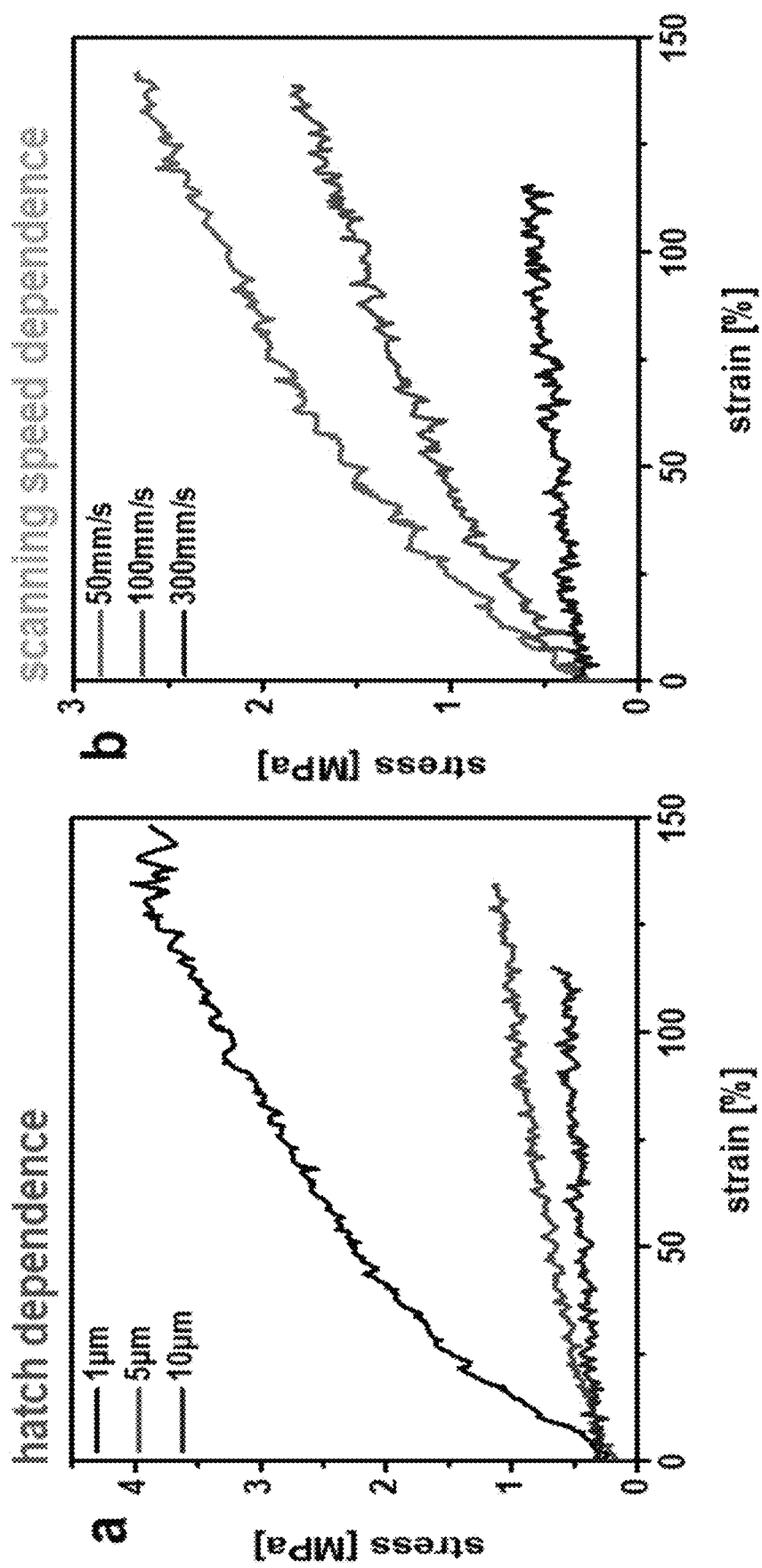
FIG. 4 shows the stress-strain behavior of the photo-polymerized self-adhesive polyurethane depending on a) the laser scanning spacing distance and b) the laser scanning speed.

In addition to the increased adhesive force, the self-adhesive polyurethane substrate became soft and flexible after adjusting the laser scanning speed and the scanning spacing distance. With regard to the stress-strain behavior shown in FIG. 4, the elasticity and ductility of the self-adhesive polyurethane substrate was confirmed by measuring the elongation at break and Young's modulus. At this time, the Young's modulus decreased as the laser scanning speed and the scanning spacing distance increased (see FIGS. 2g and 2h). Similarly to the improved adhesive force, when the laser scanning spacing distance was decreased, the Young's modulus was decreased by a factor of 10 from 2.44 MPa to 0.245 MPa, but when the laser scanning speed was decreased, the Young's modulus was decreased by a factor of 6.4 from 1.57 MPa to 0.245 MPa.

The elongation at break decreased as the laser scanning speed and the scanning spacing distance increased, and it decreased at a similar rate up to 115.4%, regardless of the increase of the laser scanning speed and the increase of the scanning spacing distance. Compared to other photopolymerizable polyurethane substrates manufactured through a conventional photo-polymerization process, the elongation at break of all photopolymerizable polyurethane substrates was reduced by a factor of about 10. The photo-polymerized self-adhesive polyurethane substrate, according to an Example of the present description, had a lower elongation at break than other elastomers, but the elongation at break was higher than the maximum strain (40 to 50%) of human epidermis. Therefore, the elongation at the break of the photo-polymerized polyurethane substrate was high enough to remain intact on the human epidermis. In addition, the photo-polymerized self-adhesive polyurethane substrate, according to the present description, exhibited a Young's modulus similar to that of human epidermis as the laser scanning speed and the scanning spacing distance increased. Therefore, it was confirmed that the adhesiveness and ductility of the photo-polymerized self-adhesive polyurethane substrate, according to the present description, were improved.

In addition, when the photo-polymerized polyurethane substrate was applied to the bent epidermis, especially the bent index finger, stable conformal contact properties were exhibited (see (d) of FIG. 2).

Figure 5:
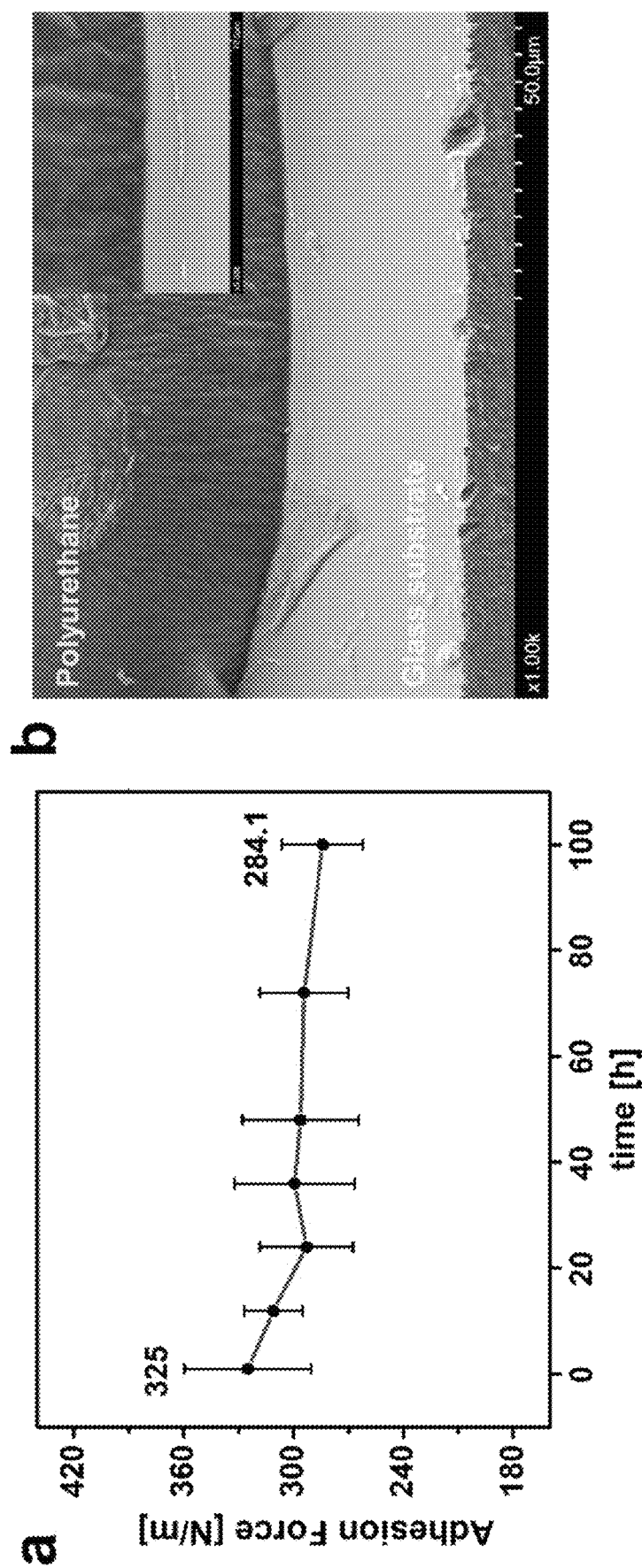
FIG. 5 shows (a) the adhesion durability of the photo-polymerized self-adhesive polyurethane substrate (Example 1) attached to a glass substrate and (b) a scanning electron microscope image of an interface between the photo-polymerized self-adhesive polyurethane substrate (Example 1) and a glass substrate.

In addition, for the evaluation of adhesion durability, the photo-polymerized self-adhesive polyurethane substrate (Example 1) was attached to the glass substrate for different durations. The measured adhesion of the photo-polymerized self-adhesive polyurethane substrate (Example 1) attached to the glass substrate decreased from 325 N/m to 284.1 N/m for 100 hours. The measured adhesive force decreased by about 13% for 100 hours, but not significantly, confirming that the photo-polymerized self-adhesive polyurethane substrate (Example 1) exhibited excellent stability and durability in adhesion (see FIG. 5).

Figure 6A:
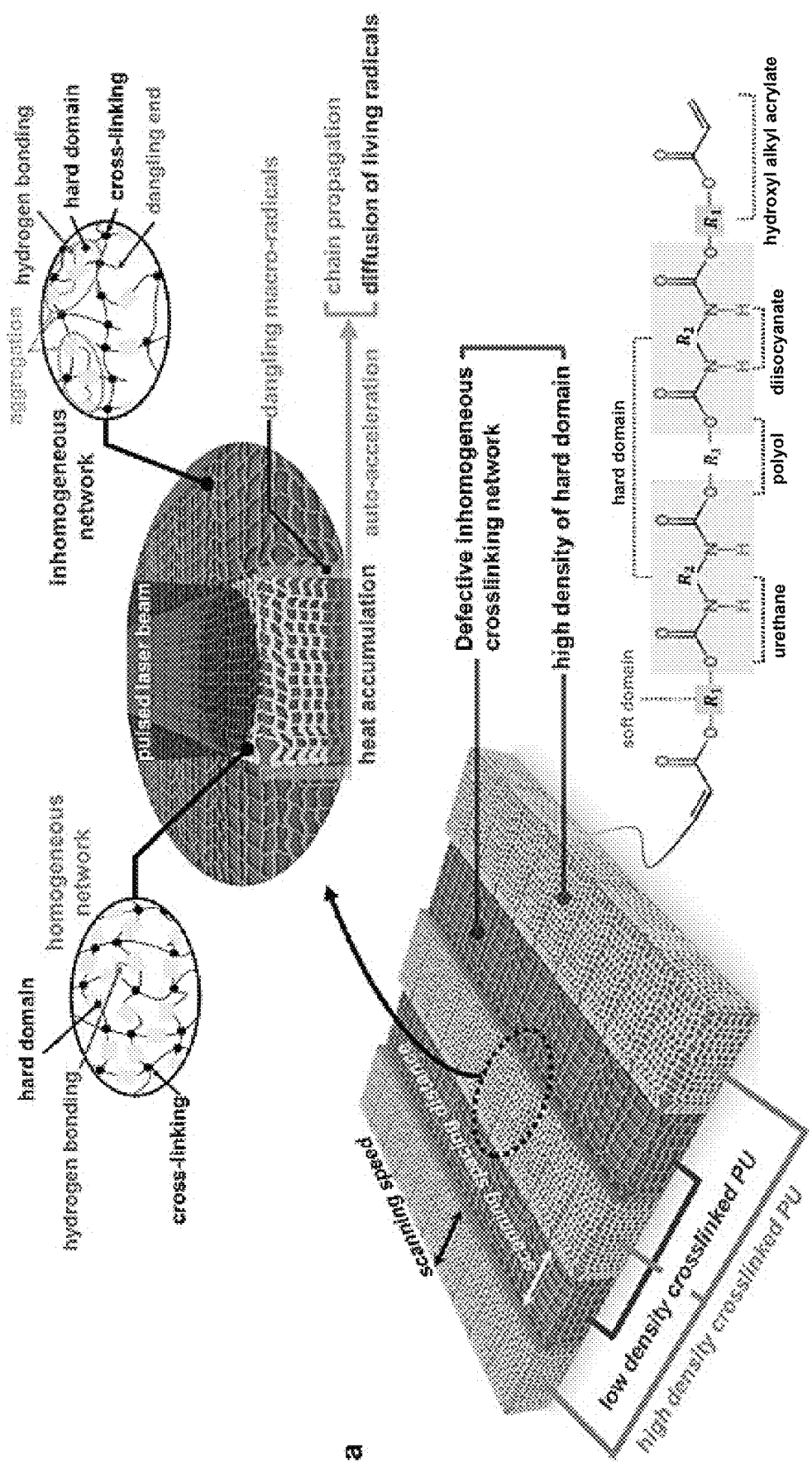
FIG. 6A shows a schematic diagram of the crosslinking network of the photo-polymerized self-adhesive polyurethane substrate from a macroscopic viewpoint and a microscopic viewpoint, and illustrates the photochemical reaction of the resin in the laser-induced photochemical reaction.

FIG. 6A shows the polymerization mechanism of different polyurethane substrates in the laser-scanned and non-scanned spacing areas. Referring to FIG. 6A, multiple reactive diphenylphosphinoyl radicals generated through TPO photolysis performed by using a pulsed laser beam in a laser-scanned area induced the formation of multiple short chains. It may be suggested that the formation of these numerous short chains instantaneously increases the crosslinking network corresponding to low mobility, resulting in the formation of highly crosslinked polyurethane in a local area. In addition, it may also be suggested that the crosslinked network is densely packed with rigid portions of polyurethane chains that affect the mechanical properties (e.g. tensile strength and Young's modulus).

Reactive macroradicals dangling from the highly crosslinked polyurethane in the non-laser-scanned spacing areas undergo chain propagation, and a small fraction of living chain radicals diffused from the laser-scanned areas can be terminated by a bi-molecular reaction. It was confirmed that these two reactions can contribute to the formation of a low-density crosslinked network with multiple defects due to chain aggregation and dangling through auto-acceleration (i.e., gel effect). In addition, it was confirmed that defective inhomogeneous crosslinking networks containing intermolecular bonds between chains and hard segments having a relatively low density can affect the mechanical and adhesive properties.

The size of the defective heterogeneous crosslinked network was controlled by modifying the laser scanning speed and the scanning spacing distance to control polyurethane polymerization through a photochemical reaction and a physical method, respectively. As for the laser scanning speed, the concentration of photo-generated radicals in a local area was modified by adjusting the irradiation time of the intense pulsed laser beam. However, as for the laser scanning spacing distance, the physical reaction area of large radical chains propagated to the unscanned spacing area was limited. As the laser scanning speed increased, the photo-polymerized polyurethane substrate exhibited a low Young's modulus and a low tensile strength through a decrease of the area of highly crosslinked polyurethane due to the decrease of the hard domain density and radical concentration that could diffuse into the unscanned gap areas. In contrast, as the laser scanning spacing distance increased, the adhesiveness and elasticity of the photo-polymerized polyurethane substrate increased due to the expansion of the defective heterogeneous crosslinked network in the non-scanned spacing areas. The presence of a defective and non-uniform crosslinked network in the unscanned spacing areas due to the laser parameter adjustment became an important point in adjusting the mechanical ductility and adhesive properties of the photo-polymerized polyurethane substrate.

Experimental Example 2: Degree of Conversion, Swelling Test and Gel Fraction

1. Evaluation Method

The degree of conversion was measured by using a Fourier transform infrared (FT-IR) spectrophotometer (Frontier, PerkinElmer). For the swelling test, a polyurethane sample (20 mm×10 mm) was kept for 7 days in a conical tube containing isopropyl alcohol (IPA). The weight of the swollen polyurethane sample was measured after saturation. The gel fraction test was performed by measuring the weight of a self-adhesive polyurethane base sample dried for 7 days at 26° C. in the air. From the measured weight, the swelling ratio and gel fraction were calculated by using the respective formulas.

2. Evaluation Results

Figure 6B:
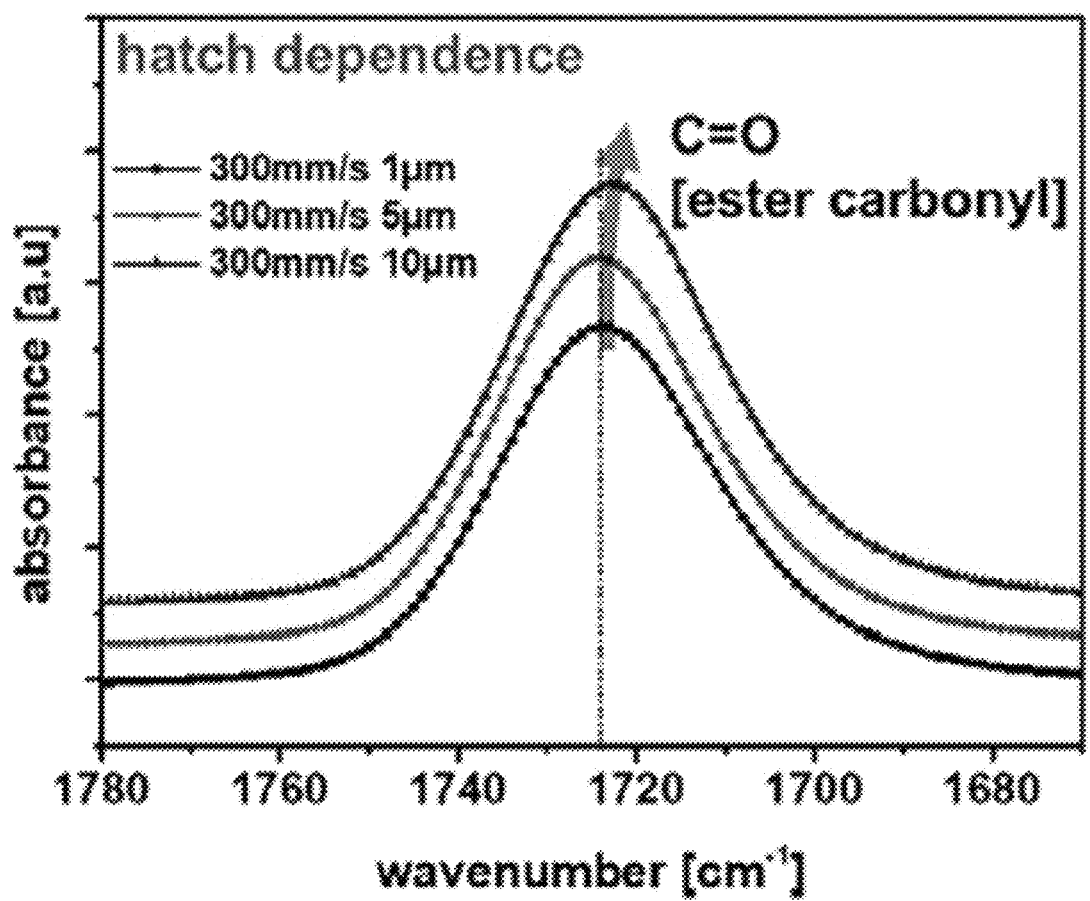
FIGS. 6B and 6C show the Fourier-transform infrared spectroscopy (FT-IR) absorption peak of the $C\!=\!O$ group (ester carbonyl) of the self-adhesive polyurethane substrates of Examples and Comparative Examples depending on the hatch spacing distance and the scanning speed.
Figure 6C:
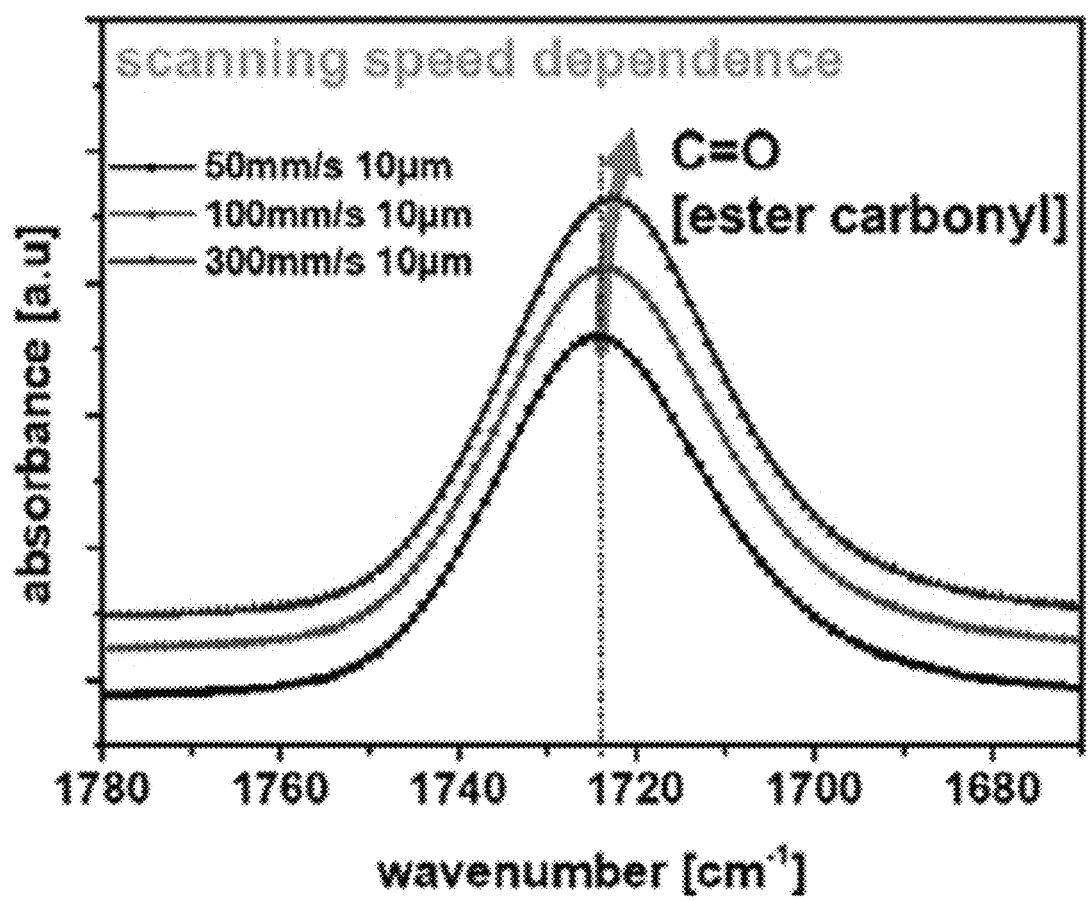
Figure 7:
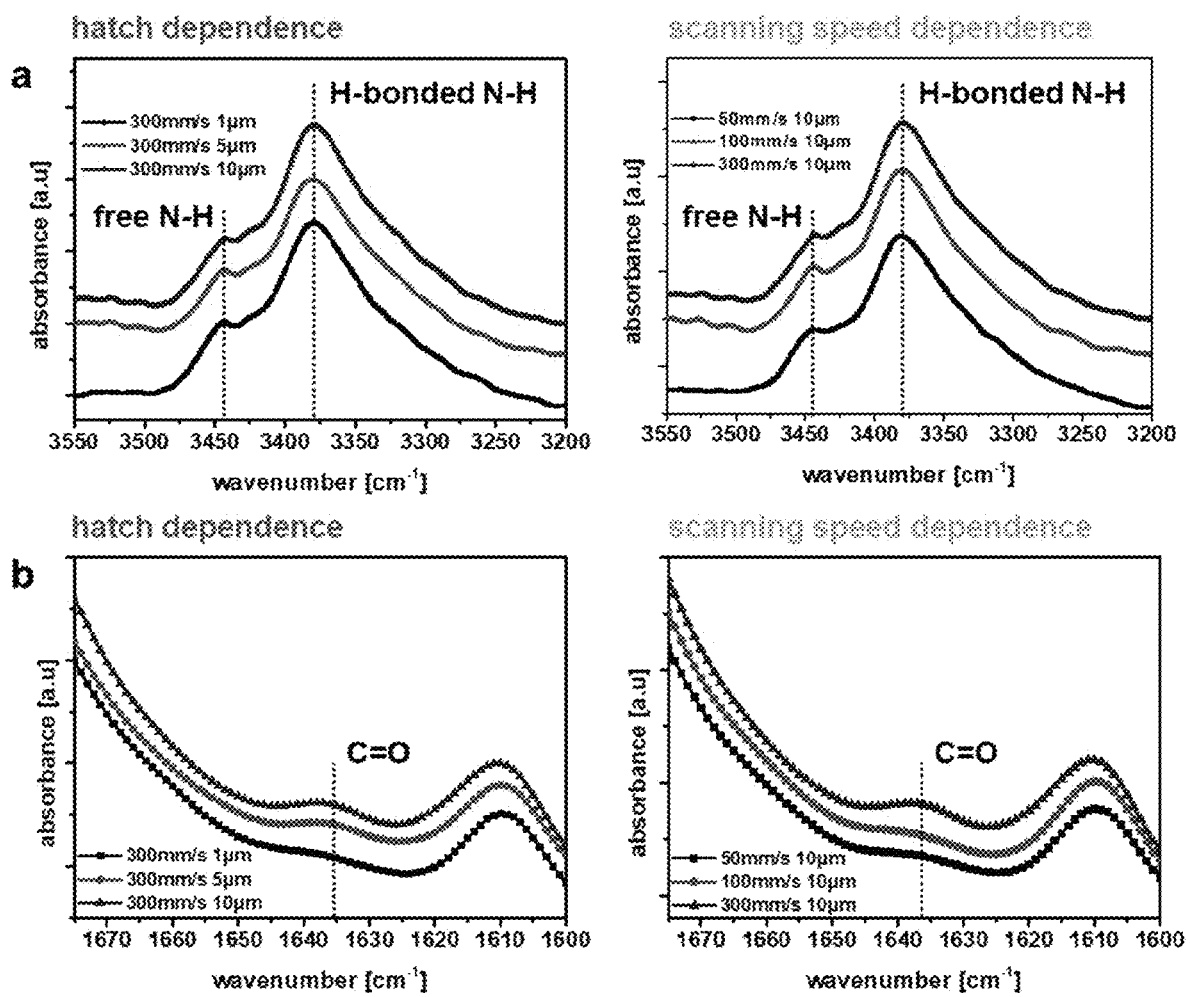
FIG. 7 shows the stretching peaks of a) free N—H and hydrogen bond N—H and b) $C\!=\!O$ of the photo-polymerized self-adhesive polyurethane substrates of Examples and Comparative Examples manufactured by using various laser parameters.
Figure 8A:
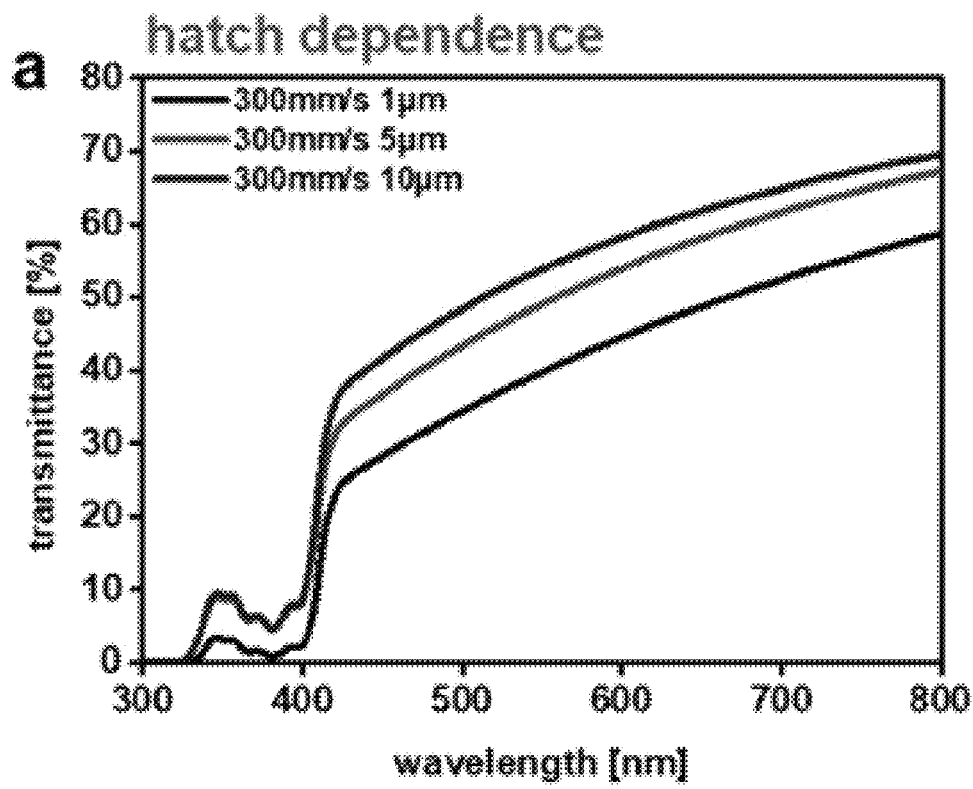
FIGS. 8A-E show the UV-Visible spectroscopy results of before (FIGS. 8A & 8B) and after (FIGS. 8C & 8D) isopropyl alcohol swelling of the photo-polymerized self-adhesive polyurethane substrates of Examples and Comparative Examples manufactured by using various laser parameters, and the digital images of the photo-polymerized self-adhesive polyurethane substrate (Example 1) before and after isopropyl alcohol swelling (FIG. 8E).
Figure 8B:
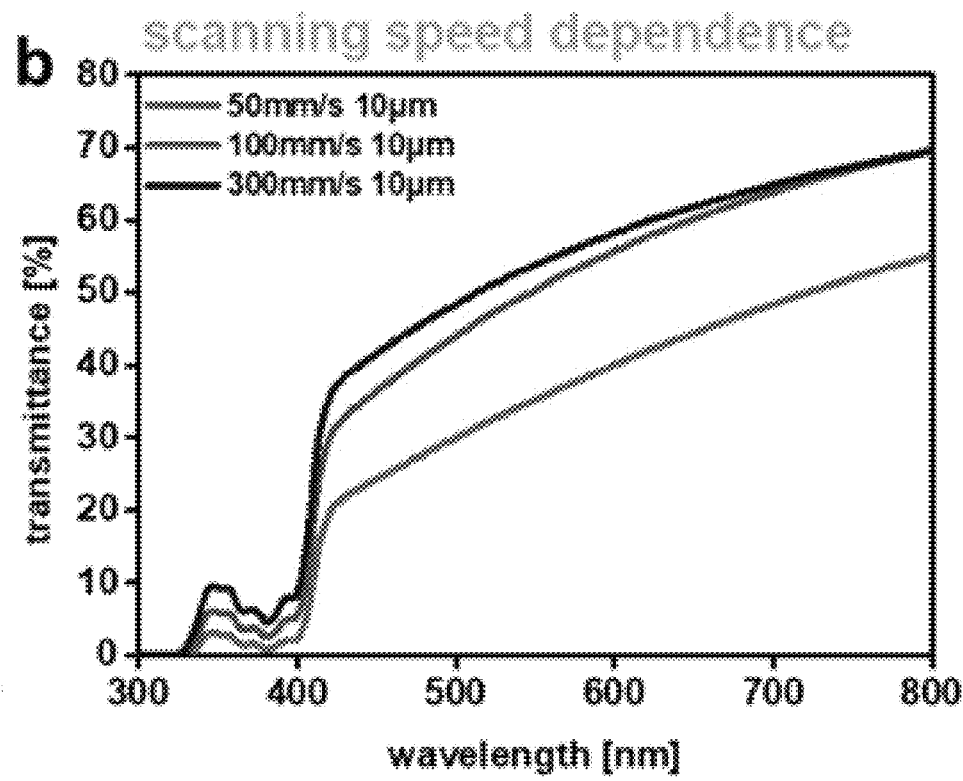
Figure 8C:
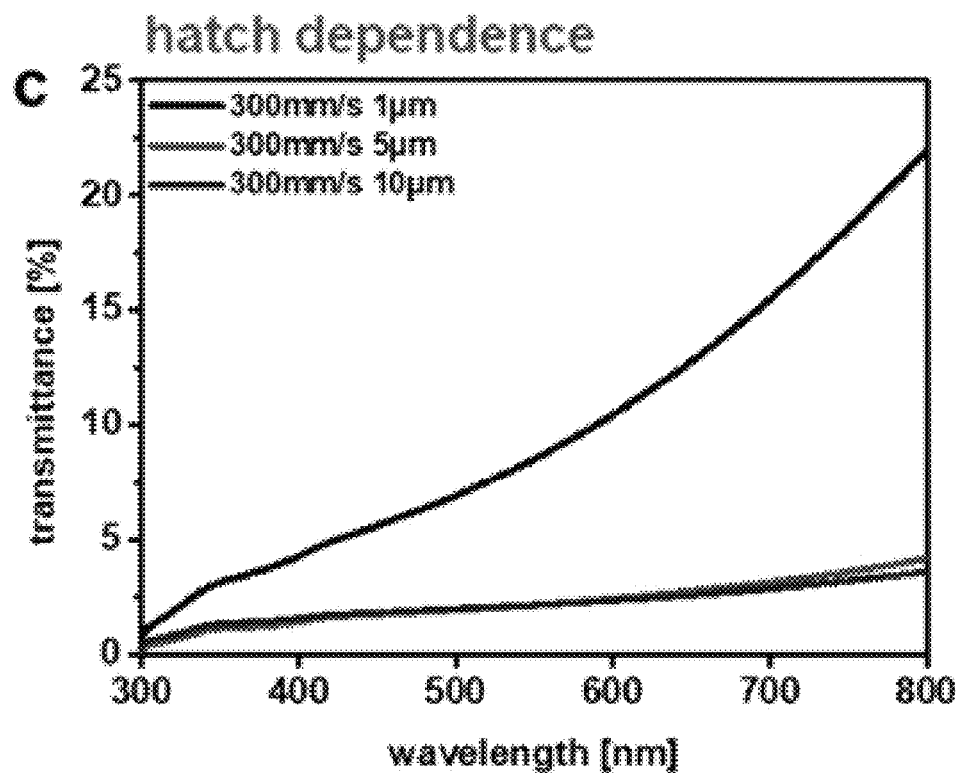
Figure 8D:
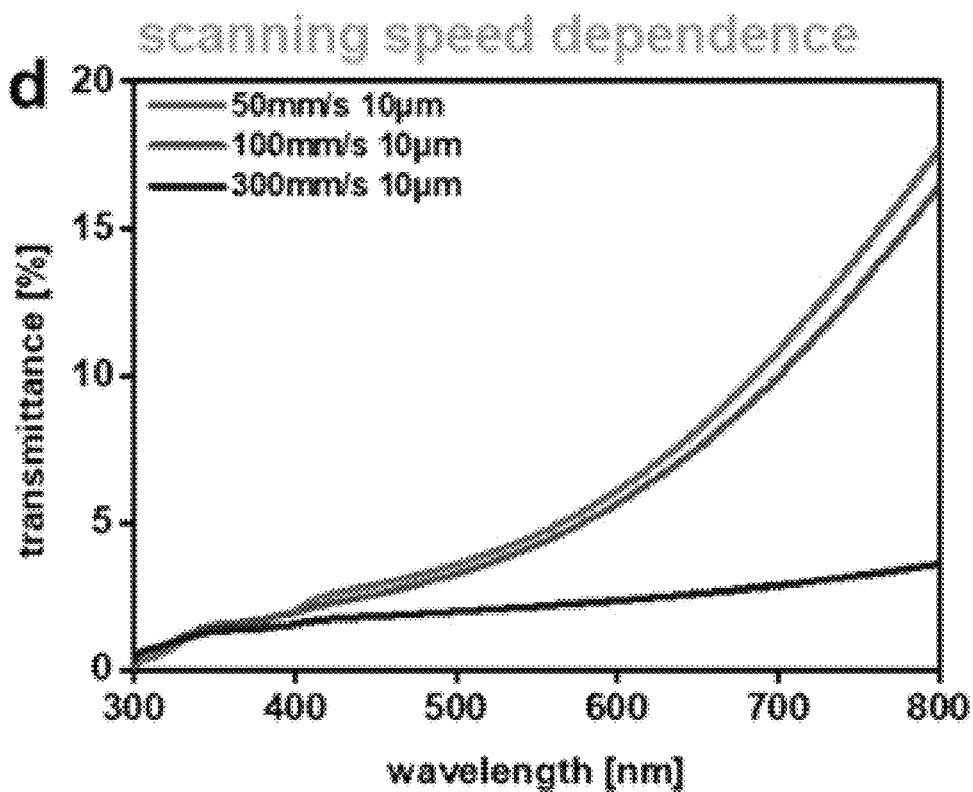
Figure 8E:

FT-IR spectroscopy was performed to confirm the consumption of intermolecular hydrogen bonds and acrylate double bonds in the photo-polymerized polyurethane substrates. Among the various vibrational modes that are sensitive to hydrogen bonding, N—H and C=O of the carbonyl group provide a lot of information. FIG. 7 shows a free N—H peak and a hydrogen bond N—H stretching peak at 3443 $cm^{-1}$ and 3380 $cm^{-1}$, respectively. Increasing the laser scanning speed and the scanning spacing distance shifted the hydrogen-bonded N—H stretching peak to lower wavenumbers, increasing the intermolecular hydrogen bonding. Similarly, FIGS. 6B, 6C, and 7 show that the C=O stretching vibration peaks at 1723 $cm^{-1}$ and 1638 $cm^{-1}$ were narrowed as the laser scanning speed and the scanning spacing distance increased and exhibited a slight shift to lower wavenumbers. As a result, it was confirmed that the shift and narrowing of the N—H and carbonyl stretching, which did not change during the photo-polymerization, represent an increase of the intermolecular hydrogen bonds obtained by the expansion of the defective heterogeneous crosslinked network as the laser scanning speed and scanning spacing distance increased.

Figure 6D:
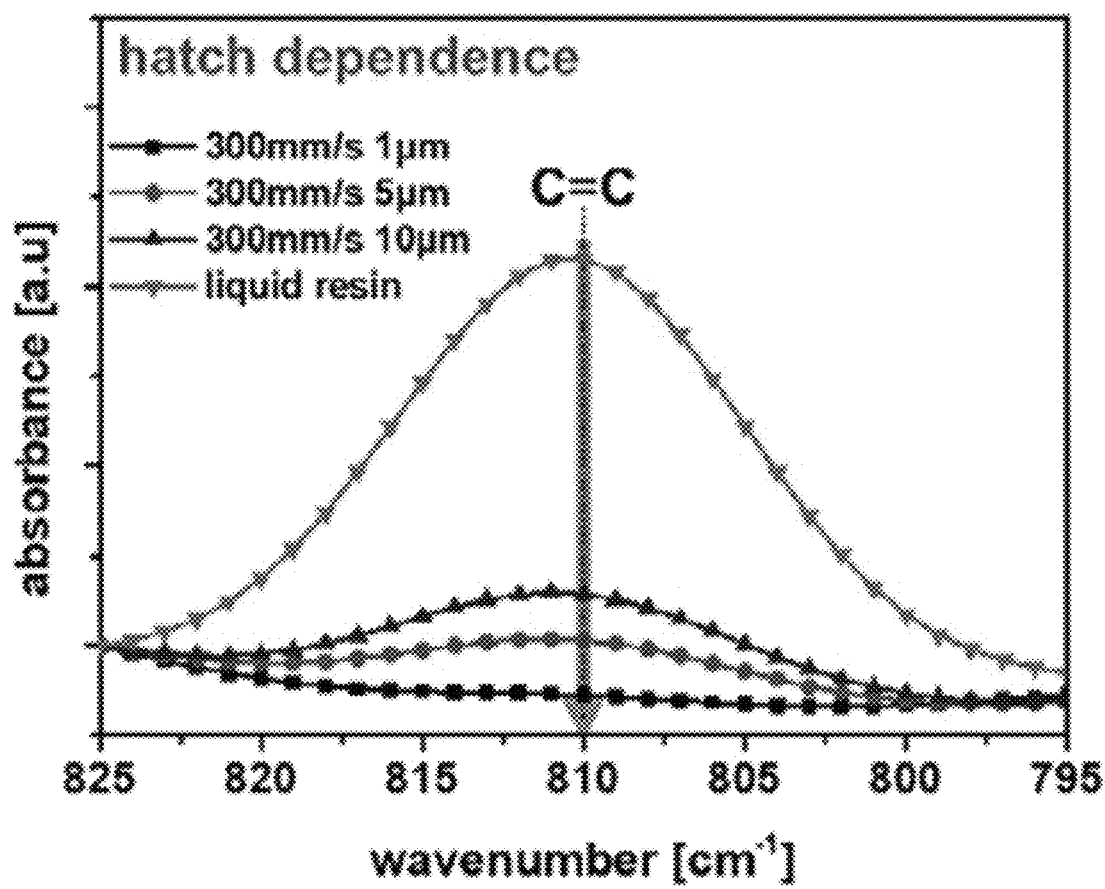
FIGS. 6D and 6E show the FT-IR absorption peaks of the $C\!=\!C$ group for the photo-polymerized self-adhesive polyurethane substrates of Examples and Comparative Examples depending on the hatch spacing distance and the scanning speed.
Figure 6E:
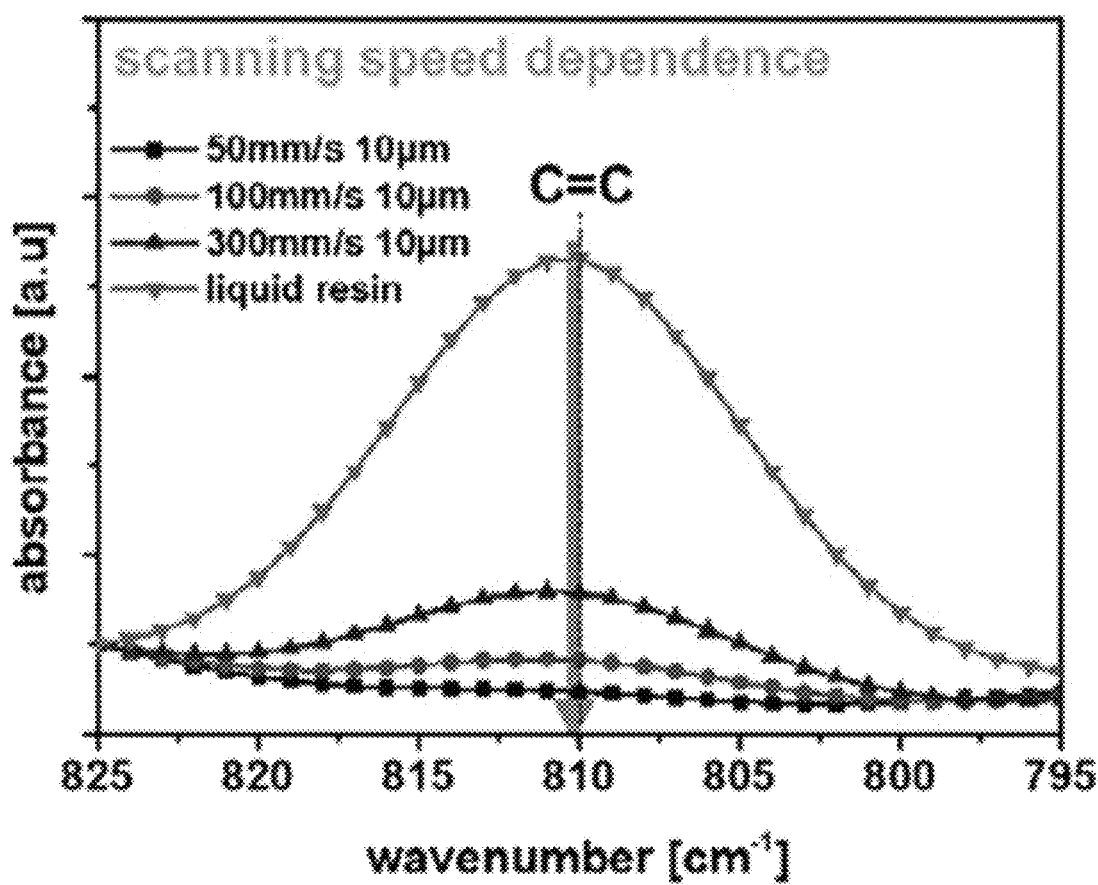

Referring to FIGS. 6D and 6E, the twisting vibrations of the $CH_2$=CH acrylate bond at the 810 $cm^{-1}$ peak consumed during the photo-polymerization increased as the laser scanning speed and the scanning spacing distance increased, while maintaining a much lower peak intensity than that of the liquid resin. Therefore, it was confirmed that the $CH_2$=CH twisting peak decreased as the photo-polymerization progressed. Therefore, it is suggested that the presence of an unreacted liquid resin or dangling terminals can cause an increase of the intensity of the $CH_2$=CH twisting peak. With regard to the presence of an unreacted liquid resin, the degree of conversion (DC) of acrylate was calculated from the C=O and C=C absorption peaks of the photo-polymerized polyurethane substrate and the liquid resin shown in FIGS. 6B to 6E by using the equation described below, and the results are shown in FIG. 6F.

[Equation 1]

$$[\text{degree of acrylate conversion}] = 100 * \times \left(1 - \frac{\text{Abs}_{PU}(C = C_{1723cm^{-1}})/\text{Abs}_{PU}(C = C_{810cm^{-1}})}{\text{Abs}_{resin}(C = C_{1723cm^{-1}})/\text{Abs}_{resin}(C = C_{810cm^{-1}})}\right)[\%] \quad (1)$$

Figure 6F:
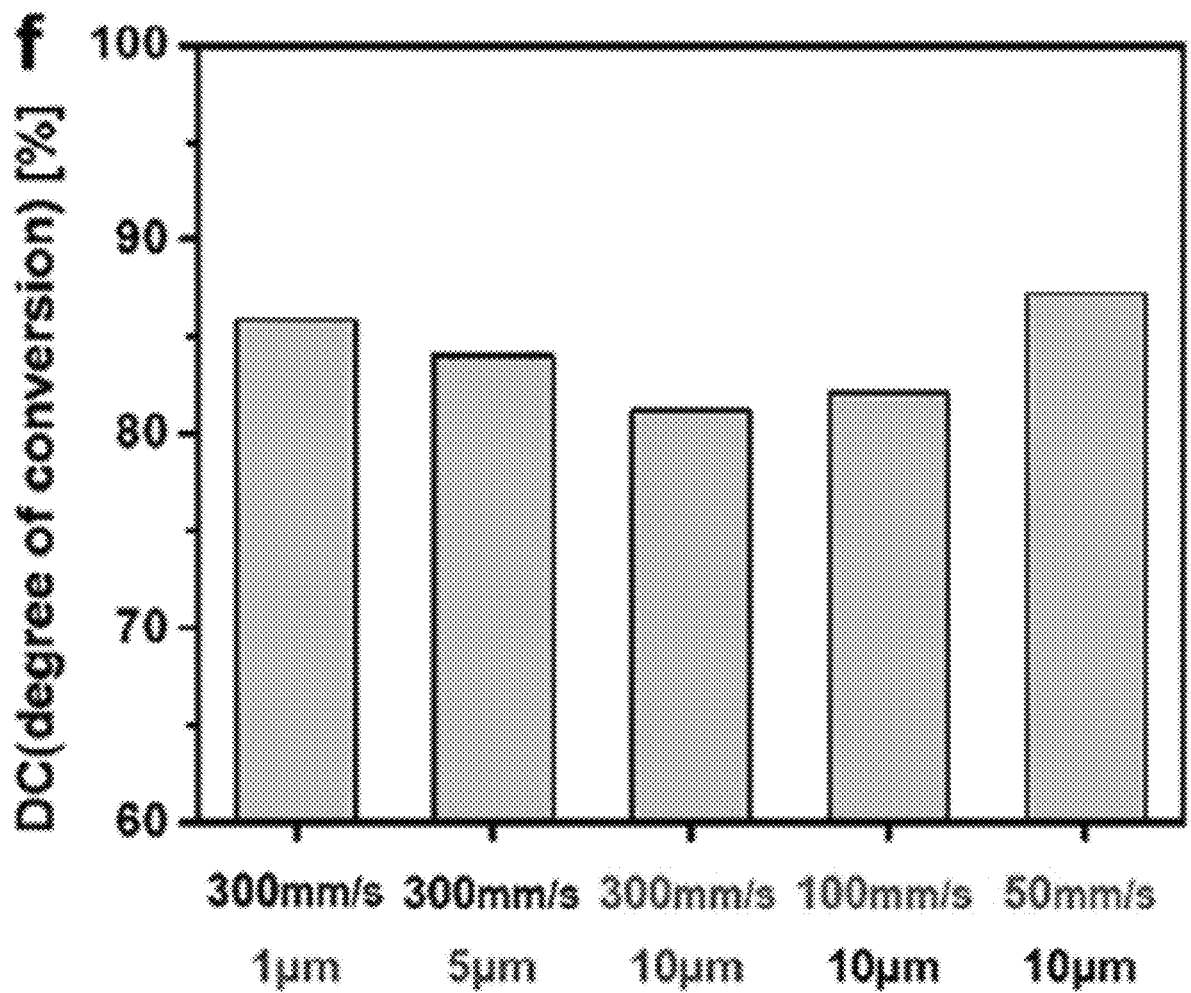
FIG. 6F shows the degree of conversion (DC) calculated from the FT-IR spectra.

Referring to FIG. 6F, the photo-polymerized self-adhesive polyurethane substrates of all Examples and Comparative Examples showed a degree of conversion of acrylate of 80% or higher. This suggests that the polymerization was completed after laser processing without a liquid resin, exhibiting a low degree of conversion of acrylate. When the photo-polymerization was conducted at an improved degree of conversion of 80% or higher in the presence of oxygen, the high intensity of the UV pulsed laser beam (891.3 kW/cm 2) generated sufficient radicals from the phosphine oxide-based photoinitiator. In addition, the low degree of oxygen diffusion of the high-viscosity liquid resin minimized the effect of oxygen.

Figure 6G:
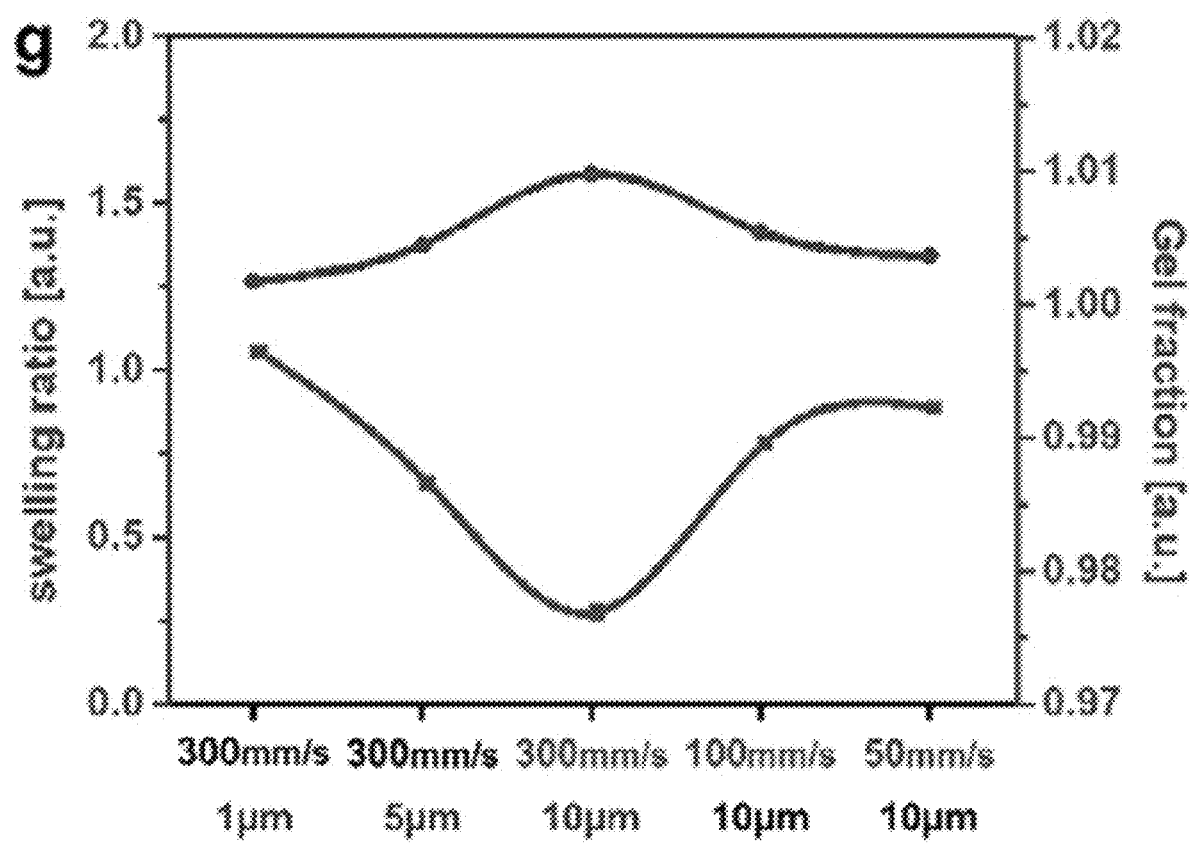
FIG. 6G shows the swelling ratio and gel fraction of the photo-polymerized self-adhesive polyurethane substrates of Examples and Comparative Examples.

Another remarkable finding is that the expansion effect of the photo-polymerized self-adhesive polyurethane substrate depended upon the laser scanning speed and the scanning spacing distance. Specifically, to confirm the swelling and sol extraction of the photo-polymerized polyurethane substrate, the weight was measured by using an isopropyl alcohol (IPA) solution. Referring to FIG. 8, it was confirmed that the photo-polymerized polyurethane substrates swollen in the IPA solution had different optical properties. The photo-polymerized self-adhesive polyurethane substrates of Examples and Comparative Examples expanded to an opaque white color as the laser scanning speed and the scanning spacing distance increased. Therefore, as the laser scanning speed and the scanning spacing distance increased, the measured swelling ratio increased, while the gel fraction decreased (see FIG. 6G). The increase of intermolecular hydrogen bonding and dangling terminals induced defects and chain aggregation in the photo-polymerized self-adhesive polyurethanes and formed defective heterogeneous crosslinked networks. The swelling behavior of the photo-polymerized self-adhesive polyurethane substrates represented the presence of a defective, non-uniform crosslinked network in the non-scanned spacing areas. Therefore, as the laser scanning speed and the scanning spacing distance increased, the defective non-uniform crosslinked network was expanded in the non-scanned spacing areas, thereby increasing the mechanical ductility and adhesive properties of the photo-polymerized polyurethane substrate allowing for conformal contact with the epidermis (see (d) of FIG. 2).

Experimental Example 3: Evaluation of Biocompatibility

1. Evaluation Method

A histological analysis was performed by using 9-week-old C57BL/6 mice. All animal experiments were performed with the permission of the Animal Use Management Committee of Kyungpook National University according to the Animal Experiment Guidelines. The mice were housed and maintained under normal conditions in a room with a light/dark cycle (based on 12 hours). To test the biocompatibility, after shaving the hair on the mouse's dorsal skin with hair removal cream (Veet), a 10 mm×20 mm photo-polymerized self-adhesive polyurethane substrate was attached to the mouse's dorsal skin from Day 1 to Day 7 (Example 1). After separating the photo-polymerized self-adhesive polyurethane substrate (Example 1), the skin area of the back of the mouse to which the photo-polymerized self-adhesive polyurethane substrate (Example 1) was attached or not attached was fixed in 4% paraformaldehyde overnight, and then embedded in paraffin for serial sectioning. After that, the skin area was deparaffinized and rehydrated. Then, the sectioned slides were stained with hematoxylin and eosin to evaluate the degree of infiltration and the epidermal thickness. Afterwards, the epidermal thickness was measured by using LAS 4.4 (Leica Microsystems).

2. Evaluation Results

Figure 9:
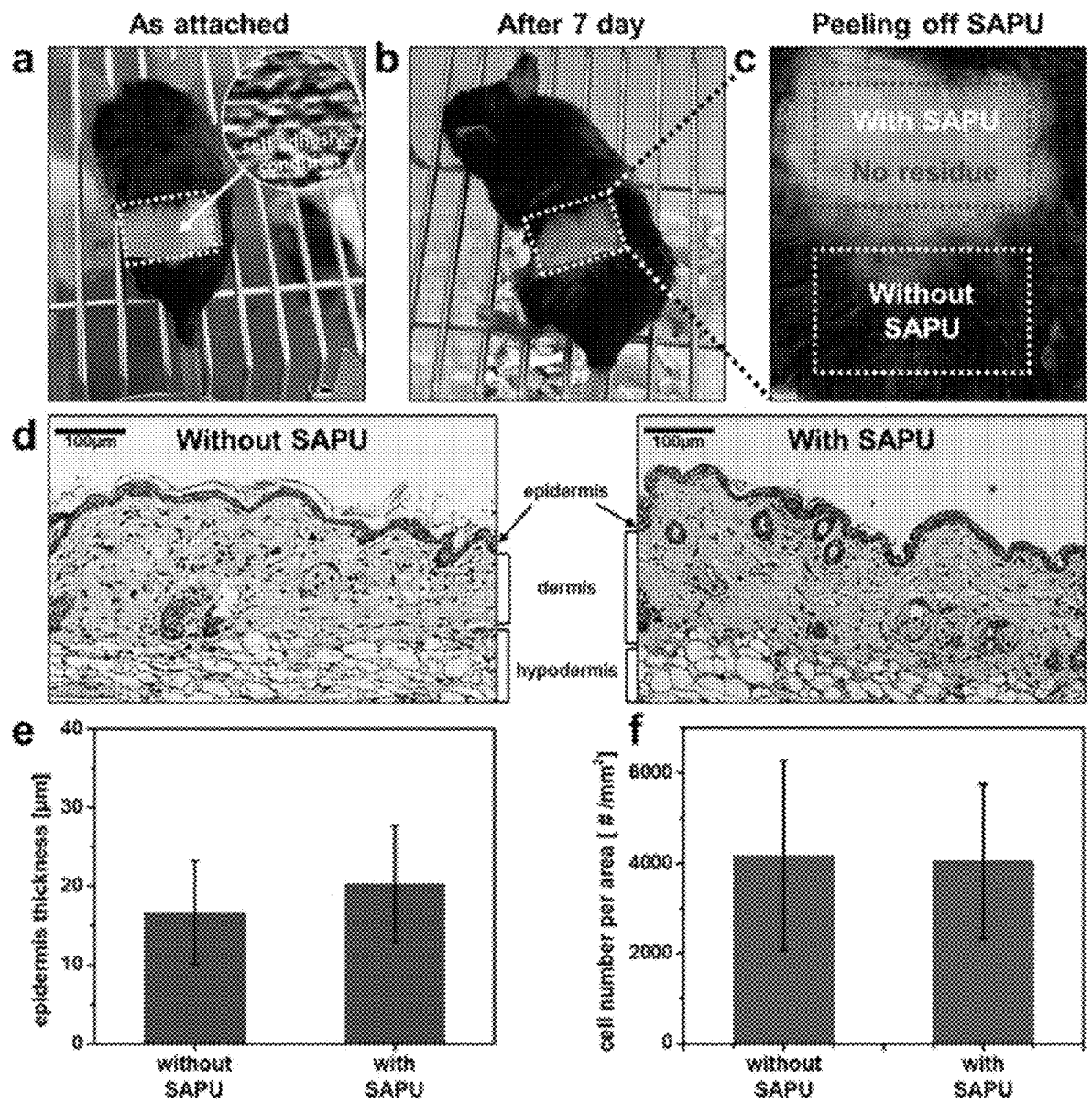
FIG. 9 shows a histological analysis of a mouse skin when the photo-polymerized self-adhesive polyurethane substrate (Example 1) was attached or not attached to the mouse skin: (a) and (b) are digital images showing the photo-polymerized self-adhesive polyurethane substrate (Example 1) attached to a shaved mouse skin from Day 0 to Day 7; (c) is a digital image showing the dorsal skin of a mouse without a residue after separating the photo-polymerized self-adhesive polyurethane substrate (Example 1) from the mouse skin; (d) is a cross-sectional image of the epidermal examination through hematoxylin and eosin staining; (e) shows the measurement results of the epidermal thickness when the photo-polymerized self-adhesive polyurethane substrate (Example 1) was attached or not attached to the mouse skin; and (f) shows the cell number per area when the photo-polymerized self-adhesive polyurethane substrate (Example 1) was attached or not attached to the mouse skin.

A photo-polymerized self-adhesive polyurethane substrate with large heterogeneous crosslinked network defects exhibits self-adhesiveness and excellent ductility. Therefore, the photo-polymerized self-adhesive polyurethane substrate according to an Example was further applied to an epidermal soft sensor support layer. Before the application to the human epidermis, to evaluate the biocompatibility of the self-adhesive polyurethane-based epidermal soft sensor, a toxicity test was performed by using animals. The biocompatibility was evaluated by attaching the photo-polymerized self-adhesive polyurethane substrate (Example 1) to the back surface of the mouse epidermis to investigate whether the photo-polymerized self-adhesive polyurethane substrate is suitable for an adhesive biosensor in the short term and long term (see (a) of FIG. 9). The photo-polymerized self-adhesive polyurethane substrate (Example 1) was attached to both sides. Therefore, one side of the photo-polymerized self-adhesive polyurethane substrate (Example 1) was covered with a commercially available adhesive tape (i.e., Magic Tape and Scotch Tape) to prevent unnecessary adhesion before a toxicity test, while the other side was attached to the mouse epidermis. The photo-polymerized self-adhesive polyurethane substrate (Example 1) attached to the mouse epidermis remained firmly adhered to the site even after 7 days. (b) of FIG. 9 showed the long-term adhesive stability of the photo-polymerized self-adhesive polyurethane substrate (Example 1).

Conformal contact between a particular substrate and the epidermis can cause contact dermatitis. Various symptoms, such as redness, itching, swelling, dryness, urticaria, and blisters may be observed on the skin. However, no visible signs of skin pathology (e.g. erythema or edema) were found on the surface of the dorsal epidermis attached to the photo-polymerized self-adhesive polyurethane substrate (Example 1) according to the present description (see (c) of FIG. 9). (d) of FIG. 9 also showed that negligible pathological changes could be observed for the photo-polymerized self-adhesive polyurethane substrate (Example 1) on the mouse epidermis. In addition, there was no significant change in the degree of infiltration of the immune cells and the epidermal thickness after 7 days (see (e) and (f) of FIG. 9). The photo-polymerized self-adhesive polyurethane substrate (Example 1), according to the present description, was confirmed to be biocompatible through the toxicity evaluation with the mouse skin.

Fabrication Example 1. Fabrication of Epidermal Soft Sensor and Sensing

To provide electrical conductivity, a silver nanowire solution in which 80 μL of silver nanowires (Ag NW, Agnw-L100, ACS material, length and diameter: 100-200 μm and 100 nm, respectively) and 94.5% ethanol was mixed was sprayed on the self-adhesive polyurethane substrate (Example 1) to form a silver nanowire network (see (c) of FIG. 1).

The skin strain sensor was restored to its initial resistance through a nanowire welding process performed by using a 355 nm ultraviolet pulsed laser. The resistance ratio measured by using the fabricated sensor was monitored by using a multimeter (34401A, Agilent Technologies) (2000, Keithley).

Experimental Example 4. Cyclic Test of an Epidermal Strain Sensor

1. Evaluation Method

A cyclic test of the epidermal strain sensor was performed by using a linear stage (X-LHM150A, Zaber) that is continuously operated for 20 times at various strains while maintaining shape recovery.

2. Evaluation Results

Applications of Self-Adhesive Polyurethane: Epidermal Soft Sensor

Figure 10A:
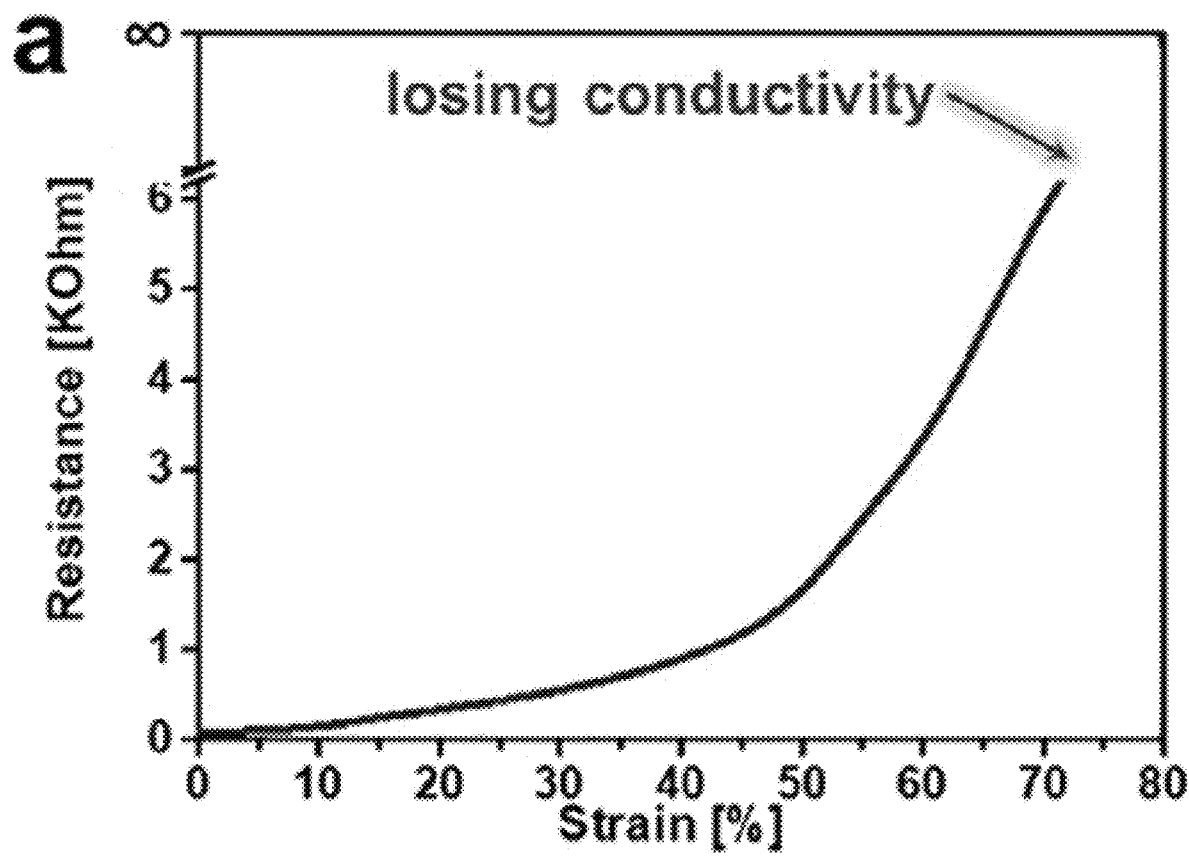
FIGS. 10A-10I show the performance of an epidermal soft sensor (Fabrication Example 1) based on a photo-polymerized self-adhesive polyurethane substrate (Example 1)
Figure 10B:
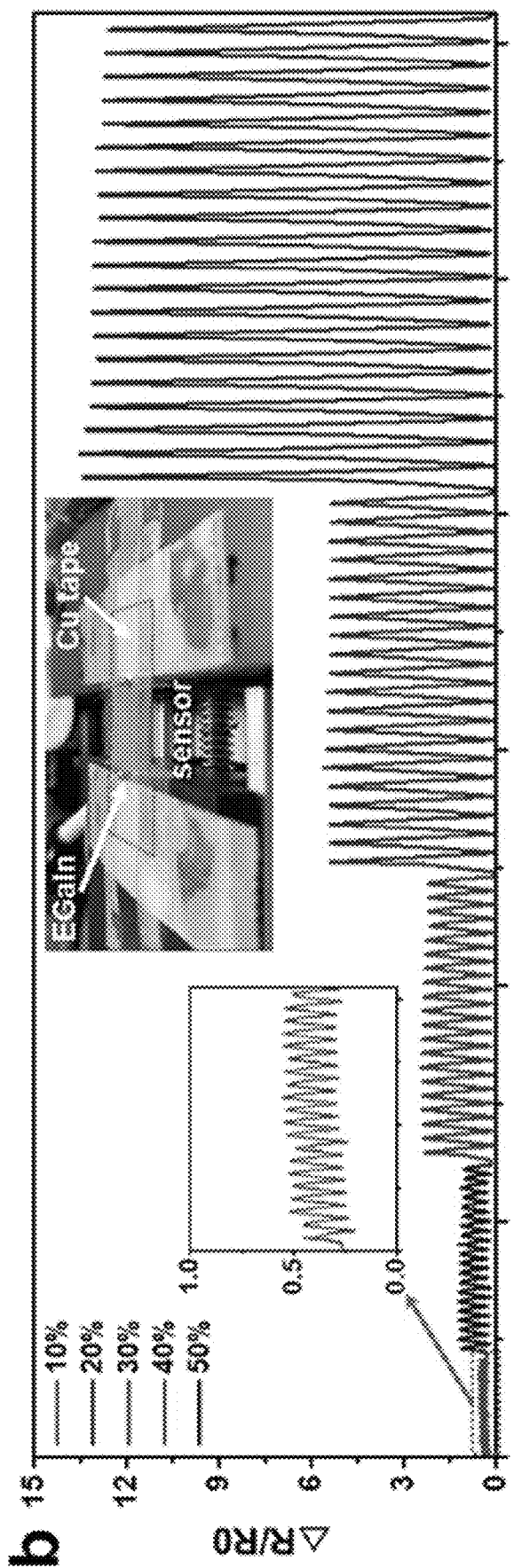

The photo-polymerized self-adhesive polyurethane substrate, according to the present description (Example 1), showed high biocompatibility. Therefore, it was applied to the fabrication of epidermal soft sensors (Fabrication Example 1) based on various photo-polymerized self-adhesive polyurethane substrates (Example 1) using Ag NW spray coating (see FIG. 10). FIG. 10A shows the electrical characteristics according to variously applied strains to the photo-polymerized self-adhesive polyurethane-based epidermal soft sensors. Interestingly, FIG. 10A showed two different slopes. The initial resistance ($R_0$=85) increased almost proportionally before 45% strain and showed a steep slope after 45% strain. Since the conductivity of the epidermal soft sensor (Fabrication Example 1) based on the photo-polymerized self-adhesive polyurethane substrate (Example 1) decreased after 70% strain due to disconnection of the silver nanowire network, the cyclic test was performed up to a maximum strain of 50%. While maintaining stable shape recovery, the epidermal soft sensor (Fabrication Example 1) based on the photo-polymerized self-adhesive polyurethane substrate (Example 1) exhibited high reproducibility and high linearity at five different strains of 10%, 20%, 30%, 40%, and 50% (see FIG. 10B).

Figure 10C:
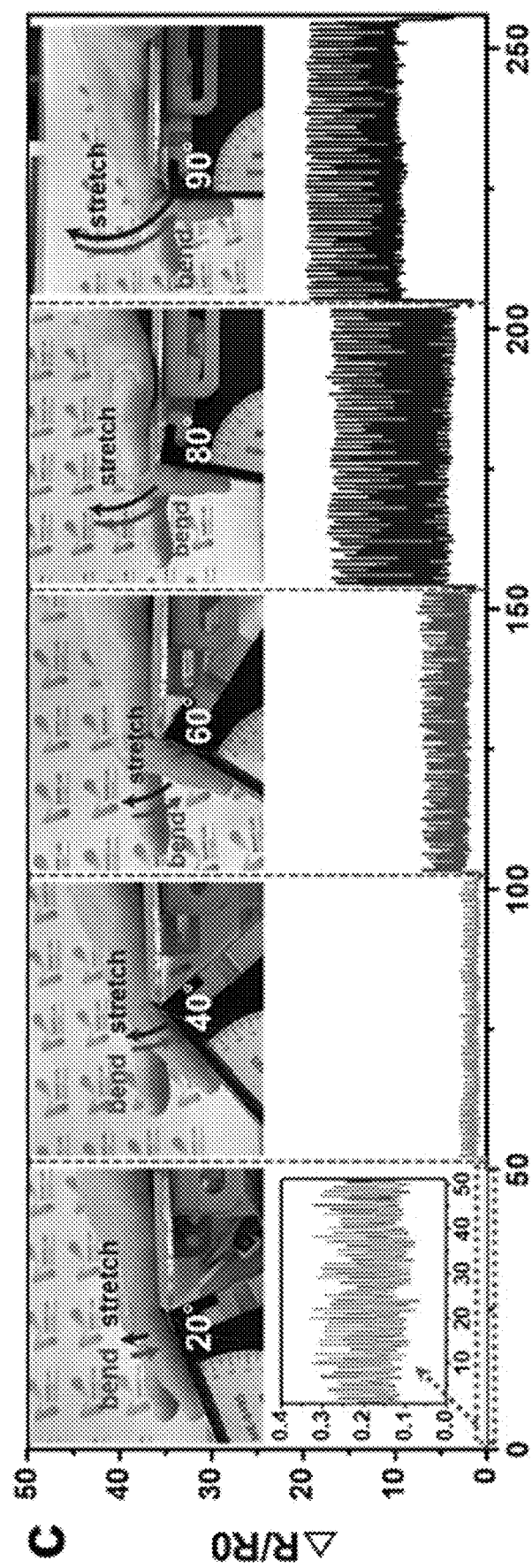
Figure 10D:
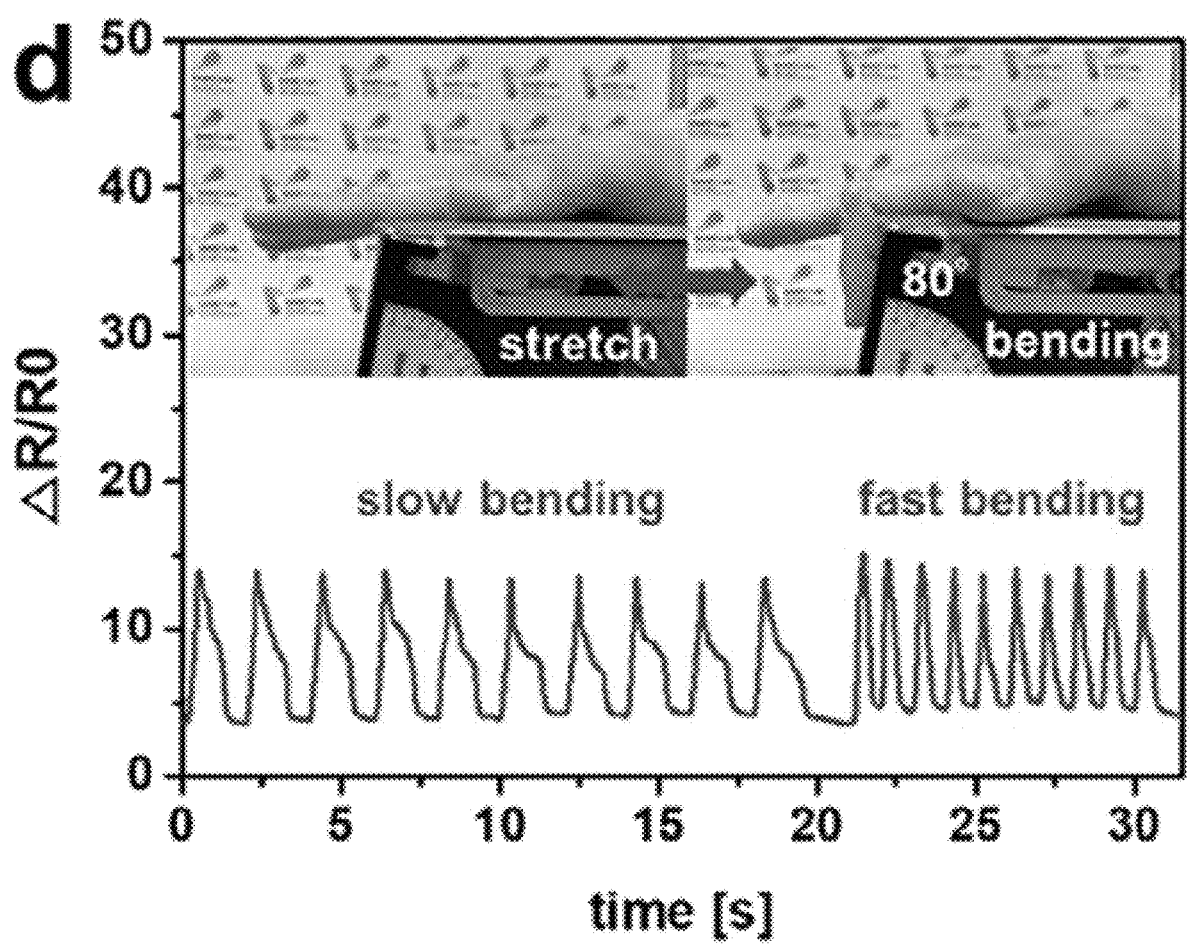
Figure 10E:
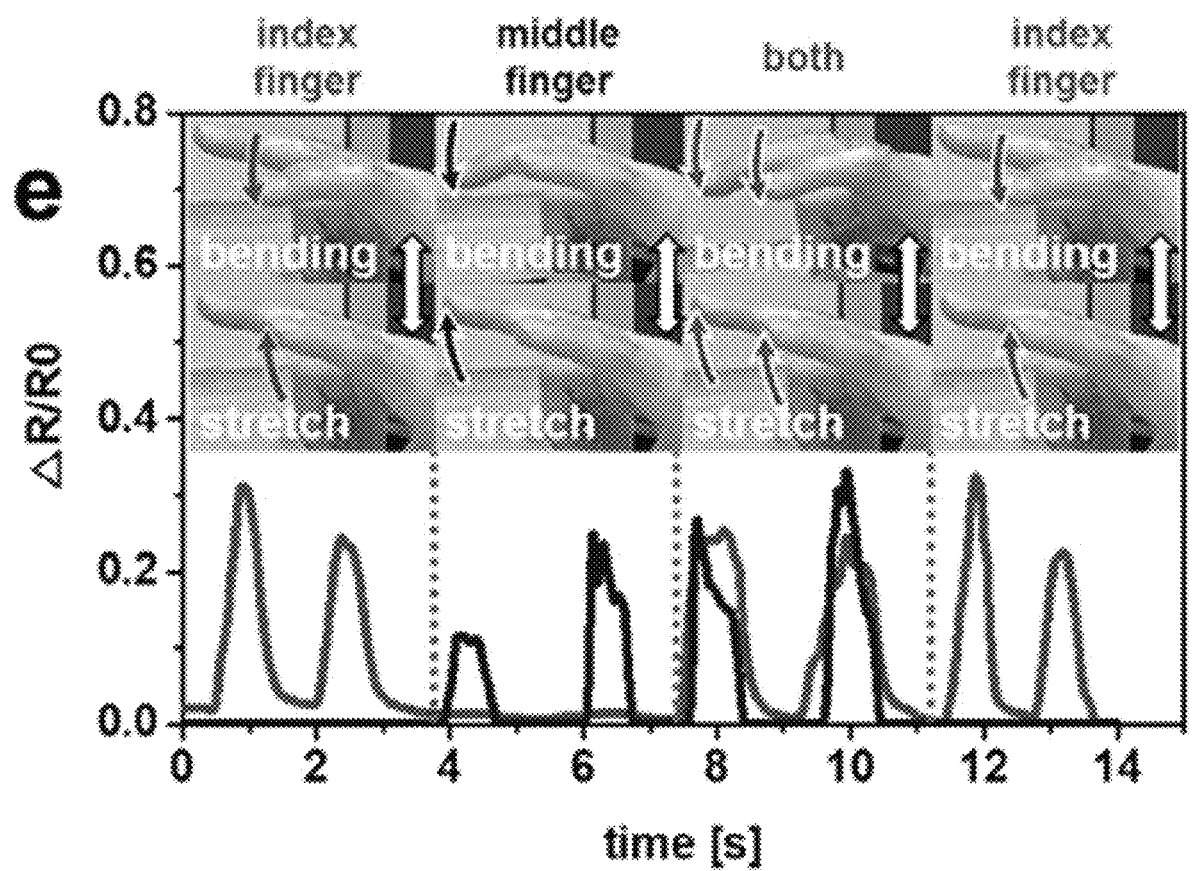
Figure 10F:
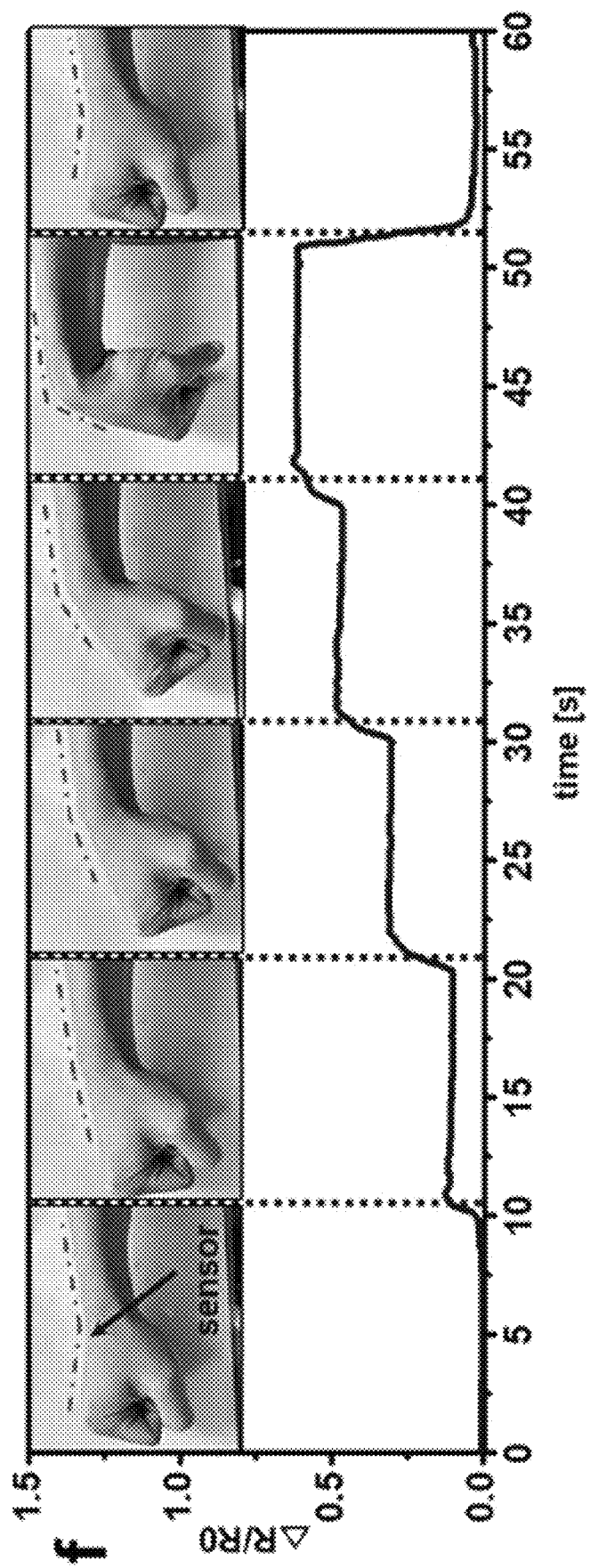
Figure 10G:
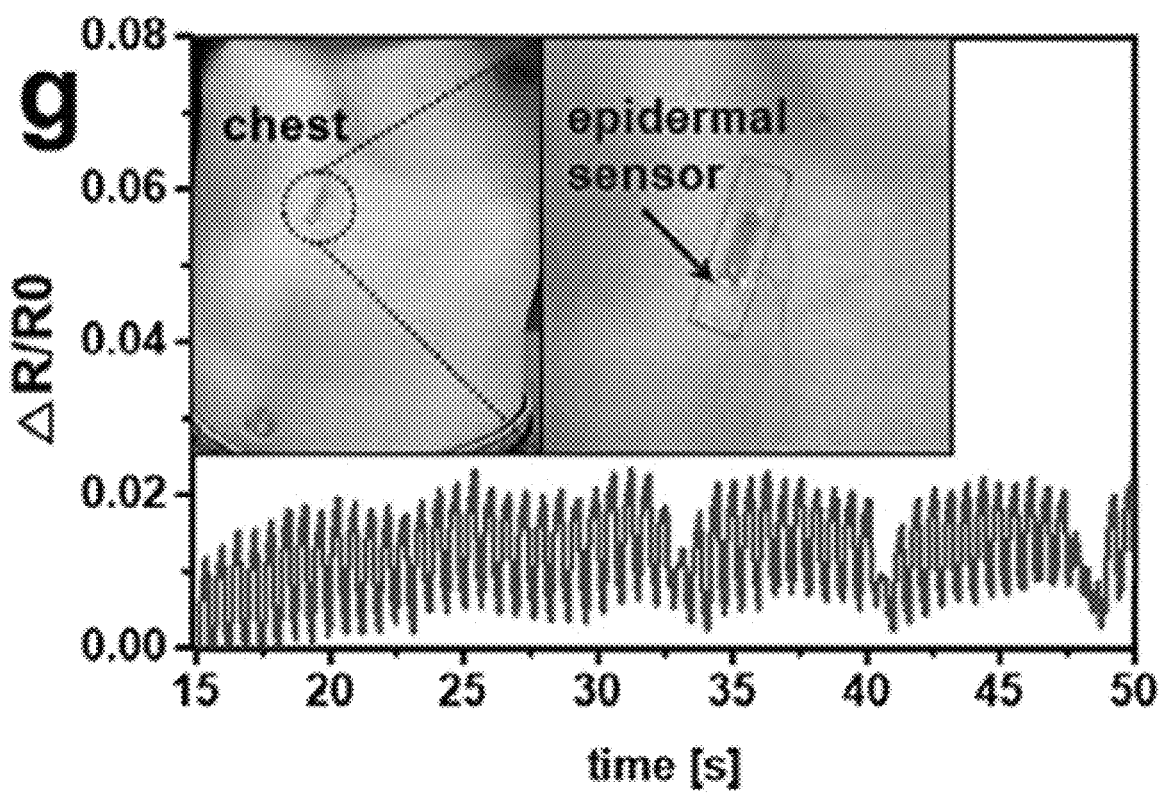
Figure 10H:
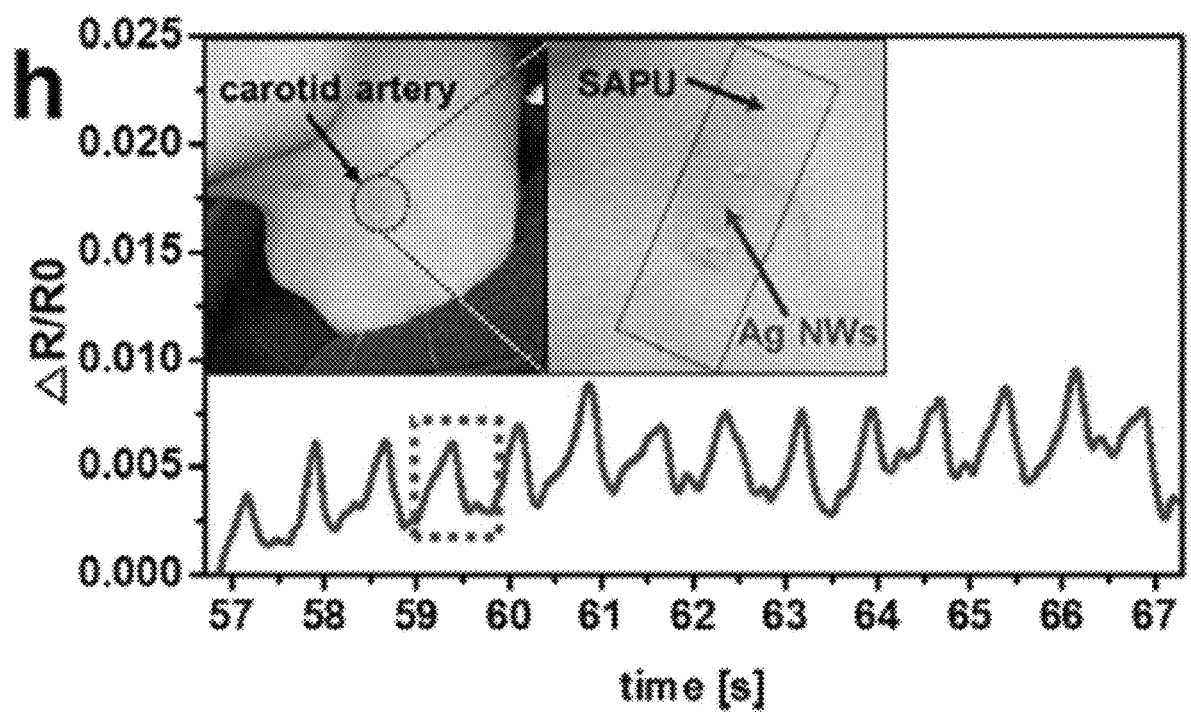
Figure 10I:
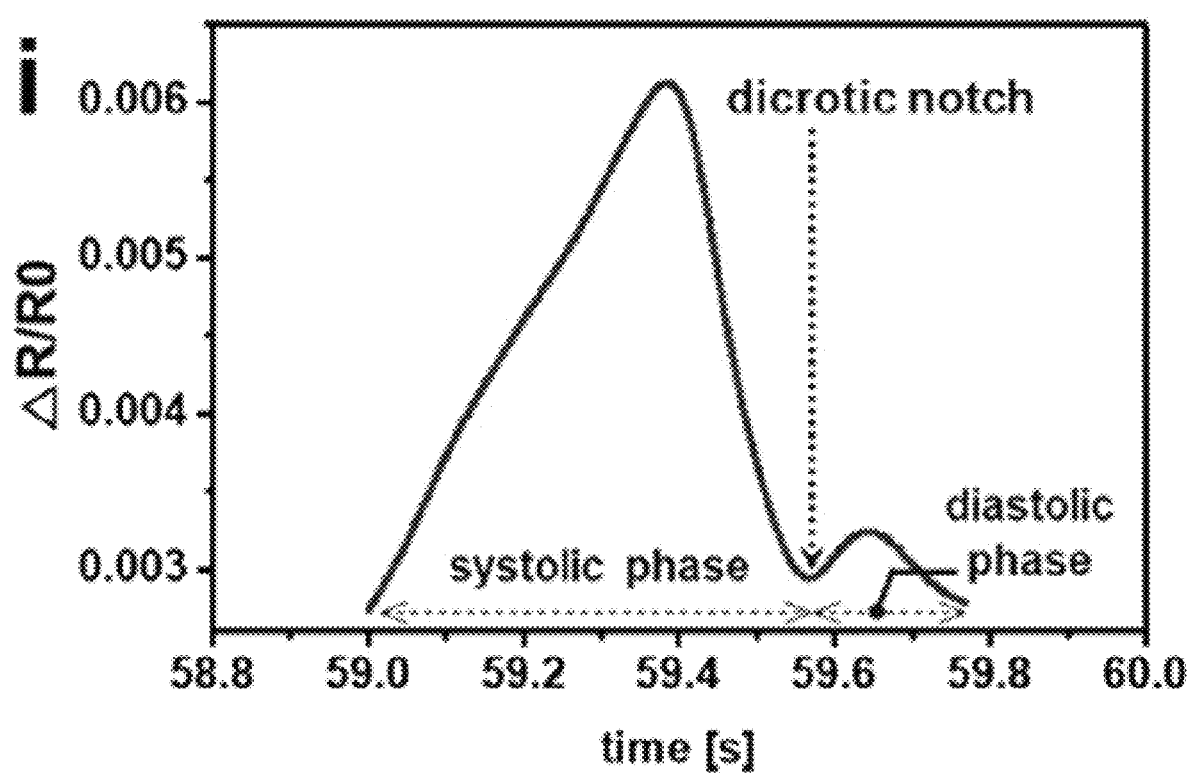

To evaluate the commercialization of the epidermal soft sensor, a cyclic test was performed by using the epidermal soft sensor (Fabrication Example 1) based on the photo-polymerized self-adhesive polyurethane substrate (Example 1) attached to a bent index finger. Referring to FIG. 10C, stable changes of electrical signals were found at various angles of the index finger (e.g., 20°, 40°, 60°, 80°, and 90°). Unfortunately, the measured electrical conductivity was not immediately recovered to the full initial resistance at an index finger angle of 60° or more because of the low recovery properties of the photo-polymerized self-adhesive polyurethane substrate (Example 1) and the buckling effect of the silver nanowire layer on the photo-polymerized self-adhesive polyurethane substrate (Example 1). However, the measured electrical conductivity showed the possibility of stable repeatability at a low bending speed of 0.5 Hz (see FIG. 10D).

Figure 11A:
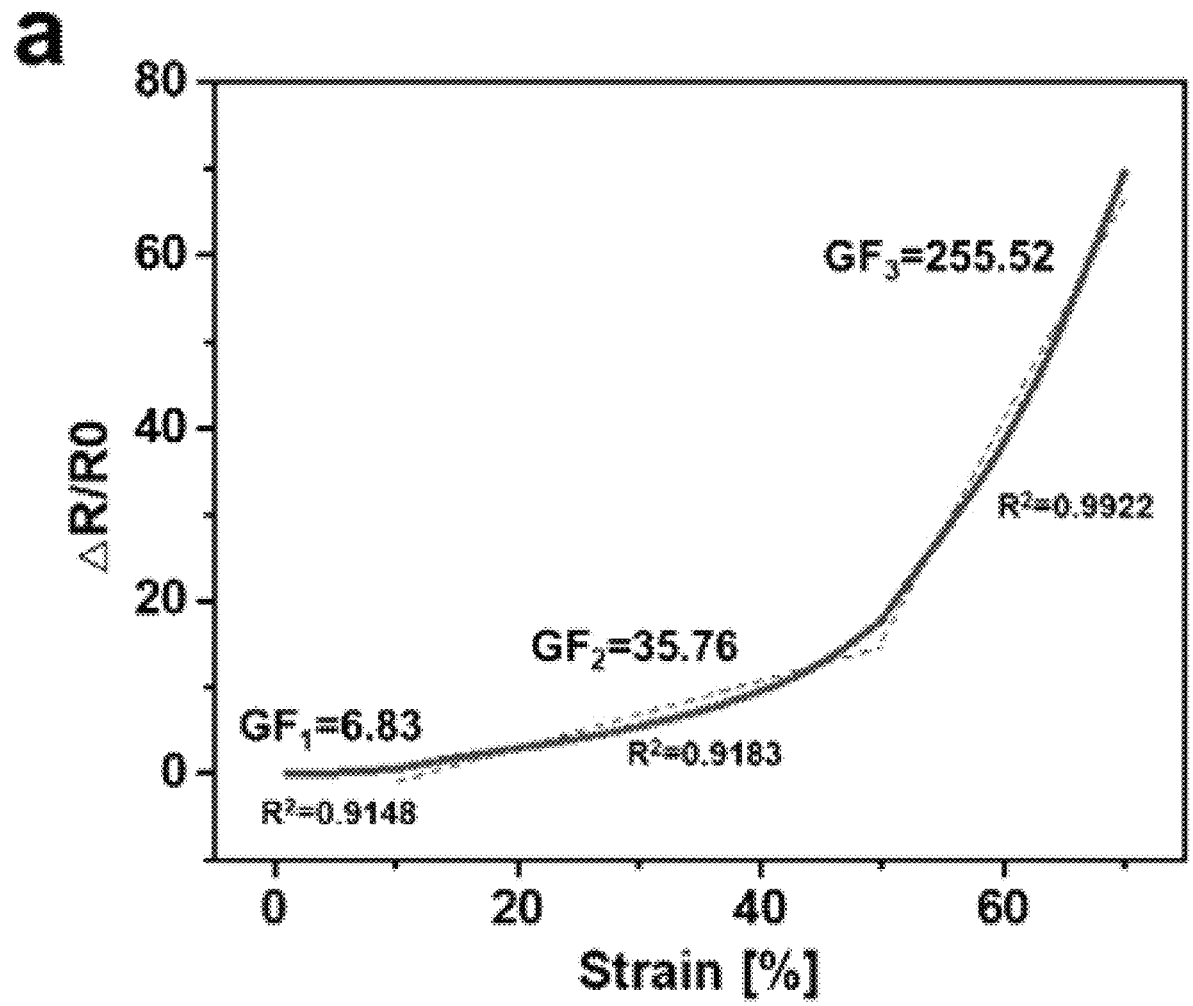
FIGS. 11A-11C show the sensitivity (11A), response time and recovery time (11B), and durability of an epidermal soft sensor (11C) (Fabrication Example 1) based on the photo-polymerized self-adhesive polyurethane substrate (Example 1).
Figure 11B:
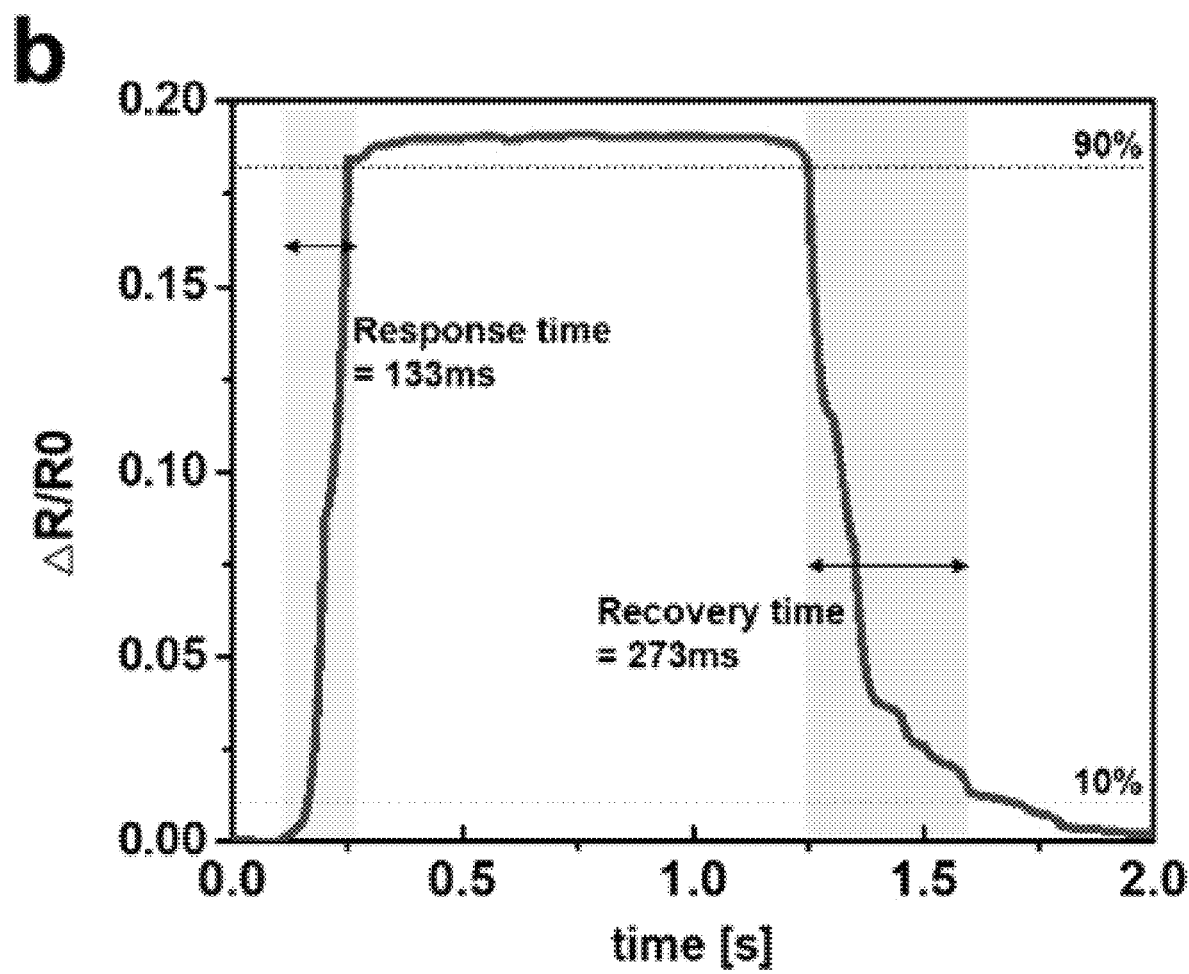
Figure 11C:
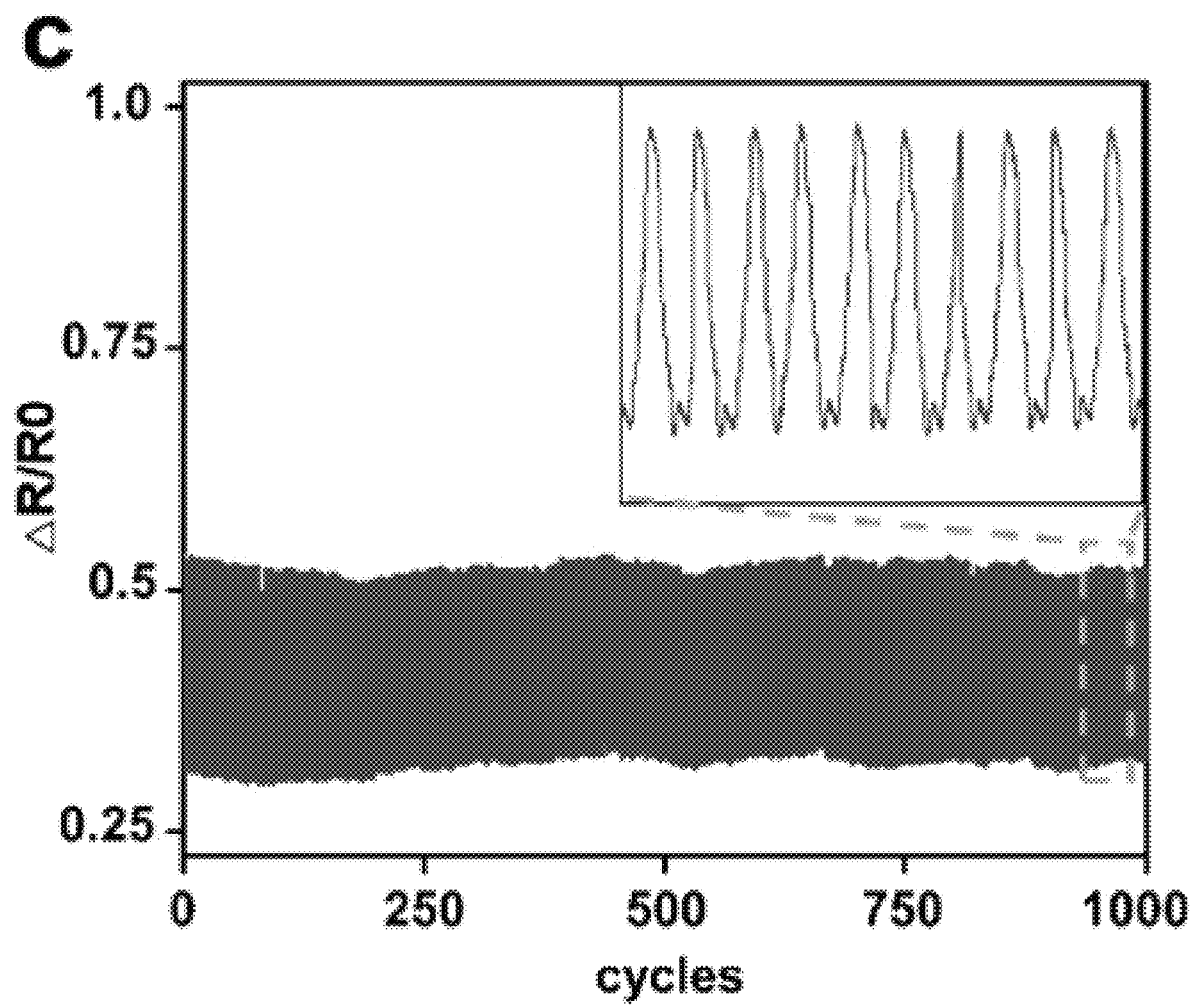

In addition, the epidermal sensing ability of the epidermal soft sensor (Production Example 1) based on the photo-polymerized self-adhesive polyurethane substrate (Example 1) is shown in FIGS. 11A, 11B, and 11C. The sensitivity was calculated by using the gauge factor GF=(R/R0)/(L/L0) (Here, R and L represent the resistance and length of the fabricated epidermal soft sensor, respectively.) The measurement showed that GF1=6.83 at 0-10% strain, GF2=35.76 at 10-50% strain, and GF3=255.52 at 50% or more strain. In addition, when the sensor was elongated at a 10% strain at a speed of 10 mm/s, the measured response time and recovery time of the sensor were 133 ms and 273 ms, respectively (see FIG. 11B).

To test the durability of the epidermal soft sensor (Fabrication Example 1) based on the photo-polymerized self-adhesive polyurethane substrate (Example 1), a cyclic stretching test was performed at a 10% strain. The measured resistance change rate was hardly changed, confirming the stable signal detection ability of the epidermal soft sensor (Fabrication Example 1) based on the photo-polymerized self-adhesive polyurethane substrate (Example 1) (see FIG. 11C).

Compared with other existing strain sensors, the epidermal soft sensor (Fabrication Example 1) based on the photo-polymerized self-adhesive polyurethane substrate (Example 1), according to the present description, showed several advantages. Despite their advantageous properties, the existing polyurethane-based strain sensors have difficulties in imparting adhesive force that is sufficient to maintain biocompatibility. In particular, unlike laser processing, the use of a UV LED lamp made the photo-polymerization difficult. On the other hand, the hydrogel-based sensor showed many advantages, such as biocompatibility, excellent elasticity, and self-adhesiveness. However, it has the disadvantage that a complicated and time-consuming process is required. On the contrary, the epidermal soft sensor (Fabrication Example 1) based on the photo-polymerized self-adhesive polyurethane substrate (Example 1), according to the present description, showed higher sensitivity and sensing characteristics at a low strain in consideration of the human skin elasticity.

In addition, the epidermal soft sensor of the present description was compared with other strain sensors using other materials. Compared to these strain sensors, the epidermal soft sensor (Fabrication Example 1) based on the photo-polymerized self-adhesive polyurethane substrate (Example 1), according to the present description, exhibited sensing performance that was not inferior despite its simple preparation method and structure.

The epidermal soft sensor (Fabrication Example 1) based on the photo-polymerized self-adhesive polyurethane substrate (Example 1) showed excellent conformal contact characteristics to human skin with high electrical sensitivity, which confirmed that it can be applied to epidermal biological signal sensor applications.

In addition, the epidermal soft sensor (Fabrication Example 1) based on the photo-polymerized self-adhesive polyurethane substrate (Example 1) detected the heartbeats (see FIG. 10G) when attached to the chest and detected the arterial pulse signals (see FIG. 10H) when attached to the carotid artery. In particular, the epidermal soft sensor (Fabrication Example 1) based on the photo-polymerized self-adhesive polyurethane substrate (Example 1) successfully detected subtle signals such as systolic and diastolic phase peaks and dicrotic notches (see FIG. 10I).

Fabrication Example 2. Fabrication of Epidermal Thermal Heater

Poly(3,4-ethylenedioxythiophene)-poly(styrenesulfonate) (PEDOT:PSS; Sigma-Aldrich) was spin-coated on a glass substrate at a speed of 750 mm/s for 1 minute.

Subsequently, 200 μL of silver nanowires were deposited on the PE-DOT:PSS layer by using a vacuum pump [TC-2000V(M), Anest Iwata Sparmax Co., Ltd.].

For a patterned shape of the silver nanowires, the silver nanowires were removed by using a UV laser at 10 mW power.

After that, a 300 μm-thick photo-polymerized self-adhesive polyurethane substrate (Example 1) was attached onto the silver nanowires under the conditions of Example 1 to fabricate an attachable epidermal thermal heater.

Experimental Example 5. Performance Evaluation of Attachable Epidermal Thermal Heater 1. Evaluation Method To measure Joule's heating of the epidermal thermal heater (Fabrication Example 2), a DC voltage was applied to the attachable epidermal thermal heater (Fabrication Example 2) by using a DC power source (E3630A, Agilent Technologies).

A thermal imaging camera (E5, FLIR) was used to measure the heat heater.

All human experiments were conducted with the permission of Kyungpook National University (Human Use and Care Committee) according to the human experiment guidelines.

The experiments were conducted with the informed consent of the subjects after acquiring the approval from all relevant ethics bodies according to all local laws.

2. Evaluation Results

In addition to various epidermal soft sensors, the photo-polymerized self-adhesive polyurethane substrate (Example 1) was applied to fabricate an attachable epidermal thermal heater (Fabrication Example 2) for thermal treatment. The photo-polymerized self-adhesive polyurethane substrate was firmly attached to the human epidermis. Therefore, the heat generated by the silver nanowires could be effectively transferred to the epidermis.

Figure 12A:
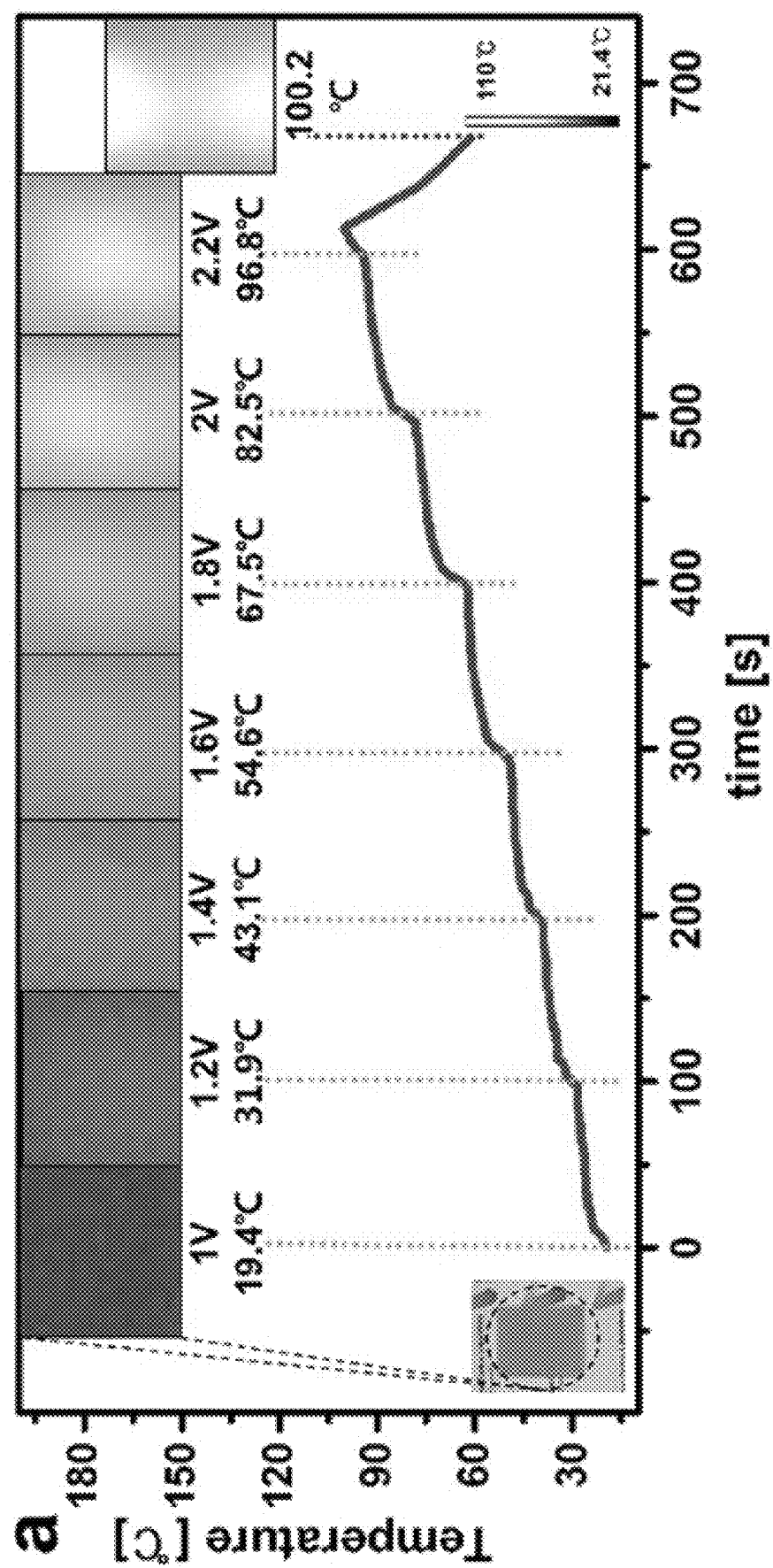
FIGS. 12A-12E show the performance of an attachable epidermal thermal heater (Production Example 2) based on the photo-polymerized self-adhesive polyurethane substrate (Example 1)
Figure 13A:
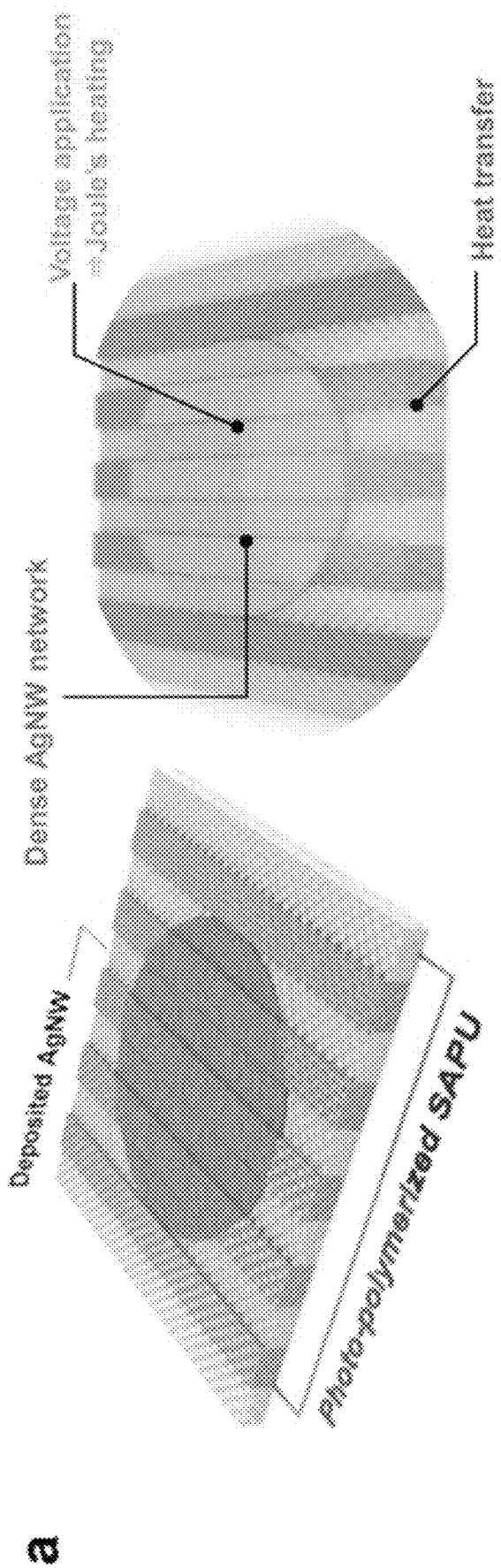
FIG. 13A is a schematic diagram of the Joule heating process of the epidermal thermal heater.
Figure 13B:
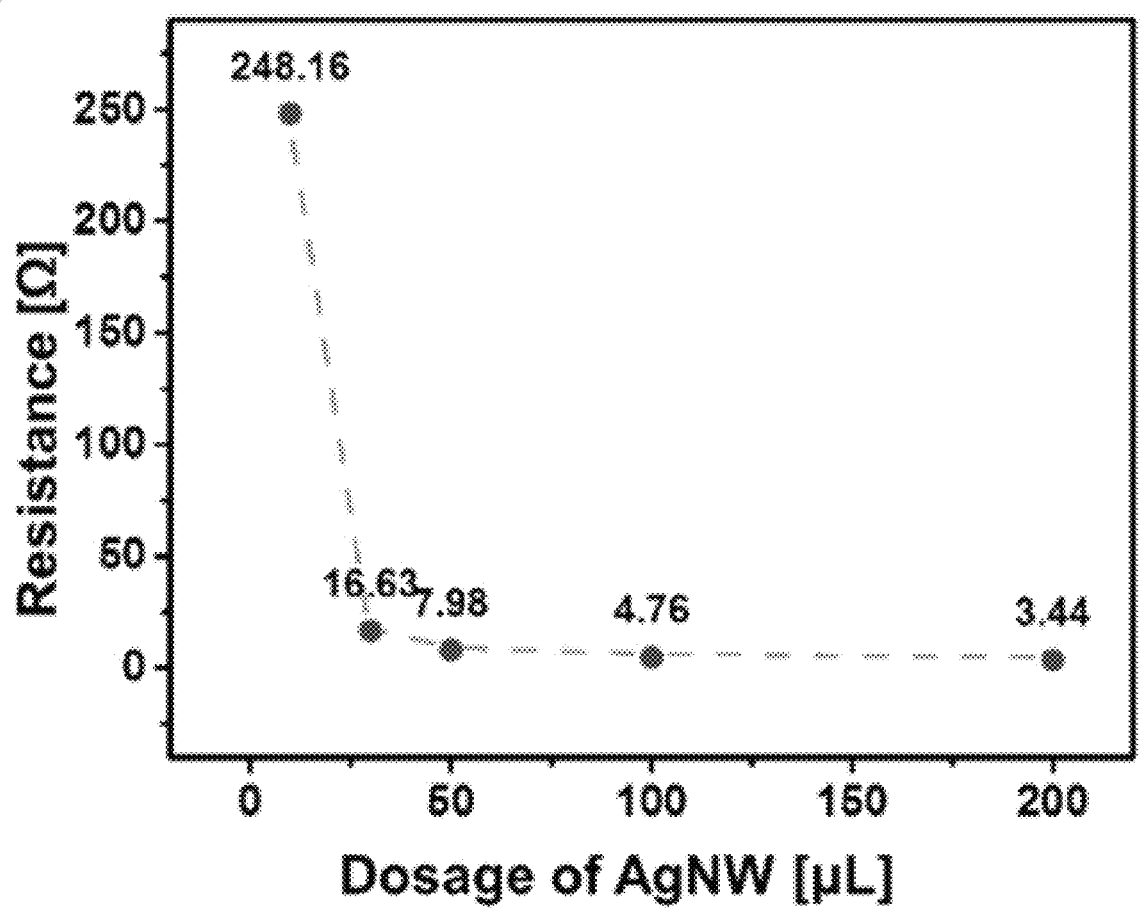
FIG. 13B shows the change of the resistance of the epidermal thermal heater depending on the amount of silver nanowires.
Figure 13C:
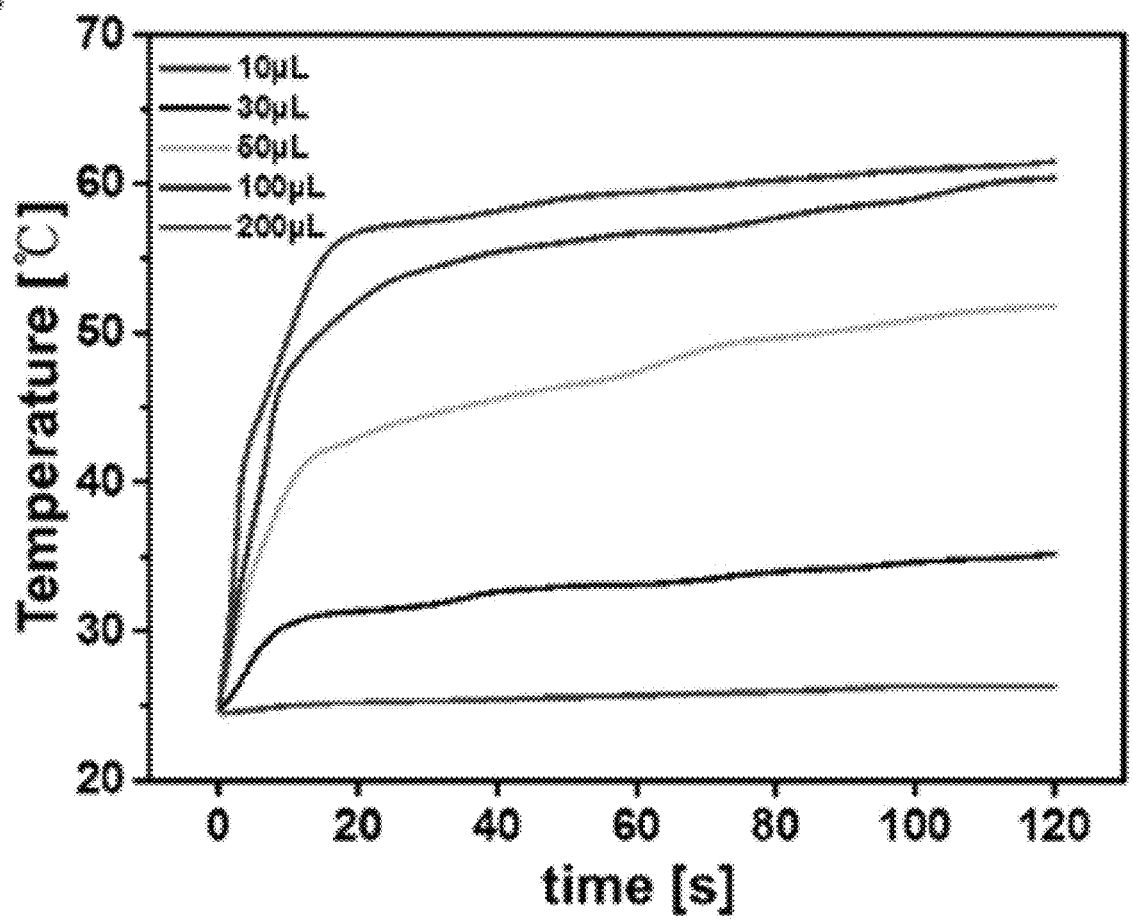
FIG. 13C shows the change of the temperature of the epidermal thermal heater depending on the various amounts of silver nanowires for 120 seconds.
Figure 13D:
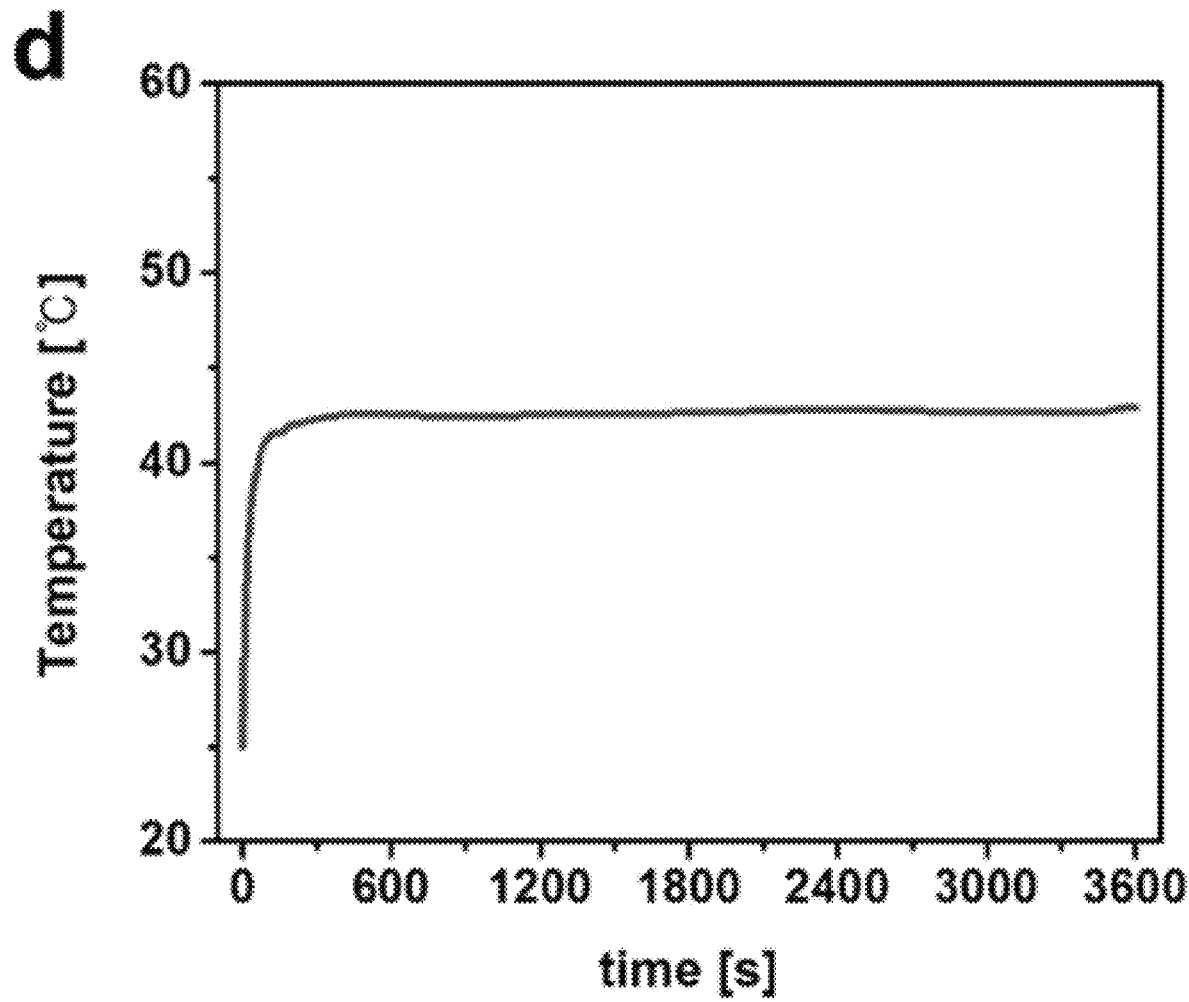
FIG. 13D shows the temperature saturation at 42.7° C. when a constant voltage was applied.
Figure 13E:
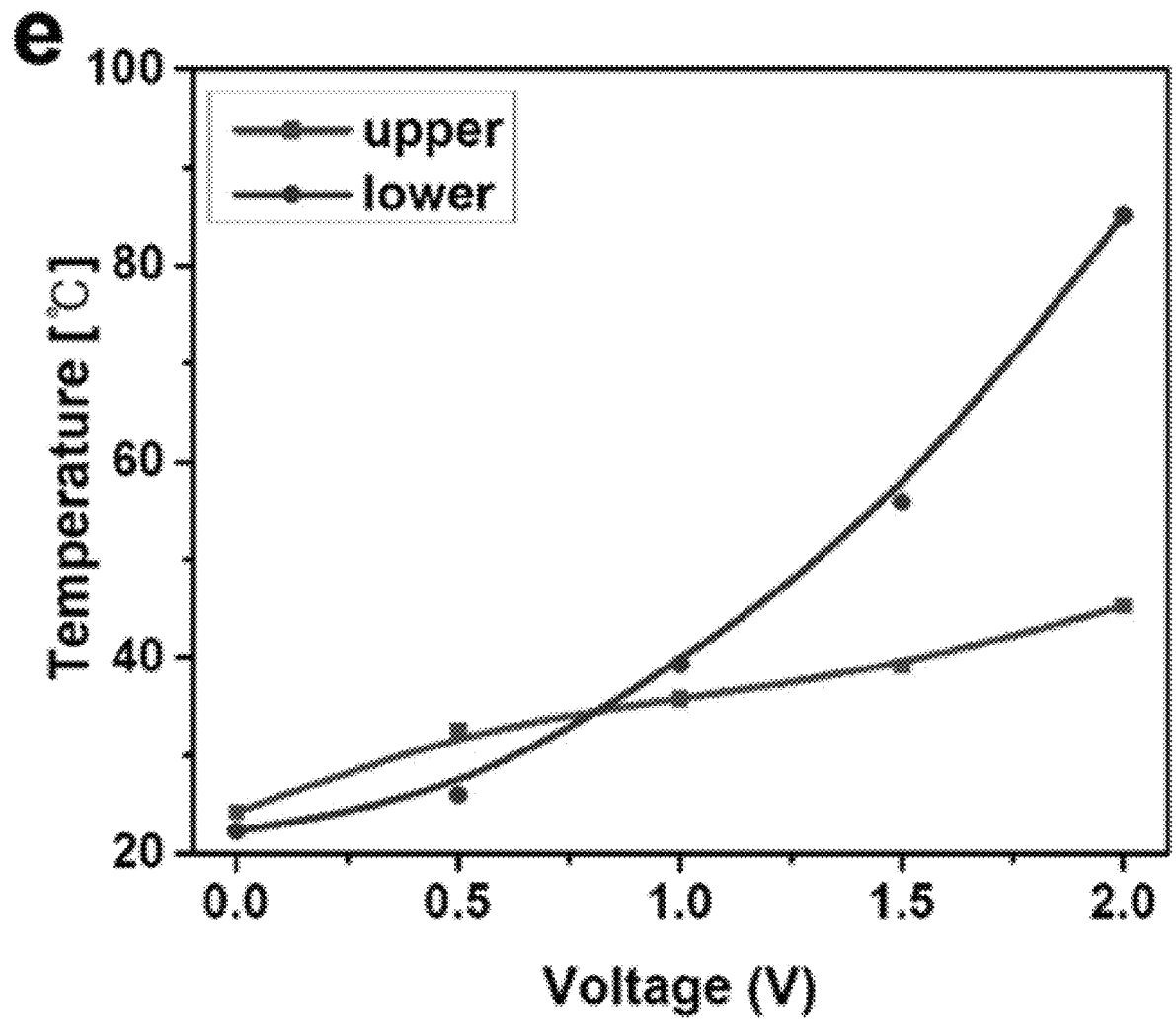
FIG. 13E shows the temperature change at the top and the bottom of the epidermal thermal heater (Fabrication Example 2) based on the photo-polymerized self-adhesive polyurethane substrate (Example 1) to which a voltage was applied.

FIG. 12A shows the temperature distribution and the change of the adhesive epidermal thermal heater (Fabrication Example 2) based on the photo-polymerized self-adhesive polyurethane substrate (Example 1) according to the applied voltage. To fabricate an attachable epidermal thermal heater, a silver nanowire network densely formed as an electrode was deposited on top of the photo-polymerized self-adhesive polyurethane substrate (Example 1) by using the vacuum transfer method. The heat generated by Joule heating of the silver nanowire electrode was transferred to the bottom surface in contact with the epidermis (see FIG. 13A). FIGS. 13B and 13C show changes in the resistance and temperature of the attachable epidermal thermal heater (Fabrication Example 2) according to the dosage of the deposited silver nanowires. The dosage of the deposited silver nanowires was fixed at 200 μl in pursuit of a stably high conductivity and temperature field in the attachable epidermal thermal heater. Therefore, when different voltages were applied, the temperature of the attachable epidermal thermal heater stably rose to 100.2° C. (see FIG. 12A). At a temperature over 100° C., the disconnection of the silver nanowires reduced the temperature of the attachable epidermal thermal heater, which was similar to the phenomenon found in previous studies. The disconnection of the silver nanowires may be regarded as a risk of the Joule heating process, but the risk was lowered due to the temperature saturation. Under the application of 1.3 V, the temperature rapidly reached the threshold in 2 minutes and was stably saturated at 42.7° C. for 1 hour (see FIG. 13D).

Figure 12B:
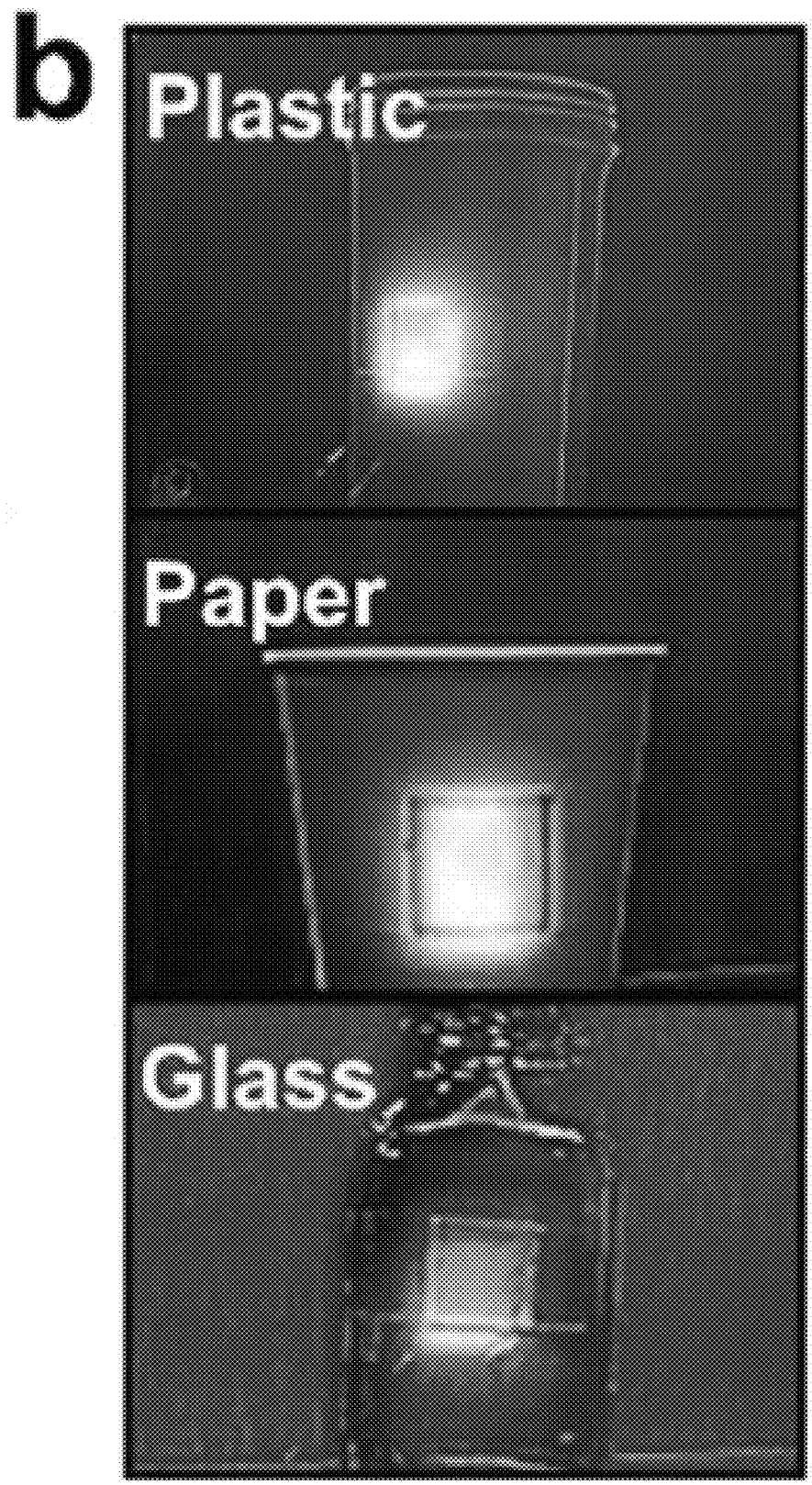

It was confirmed that the attachable epidermal thermal heater (Fabrication Example 2) based on the photo-polymerized self-adhesive polyurethane substrate (Example 1) can be conformally attached to any material (e.g. plastic, paper, and glass) that serves as a thermal heater. was confirmed (see FIG. 12B). The photo-polymerized self-adhesive polyurethane substrate manufactured according to an Example (Example 1) showed high biocompatibility and excellent conformal contact properties. In addition, despite the relatively low thermal conductivity of polyurethane, the heat generated from the silver nanowires of the attachable epidermal thermal heater was efficiently transferred to the epidermis.

Figure 12C:
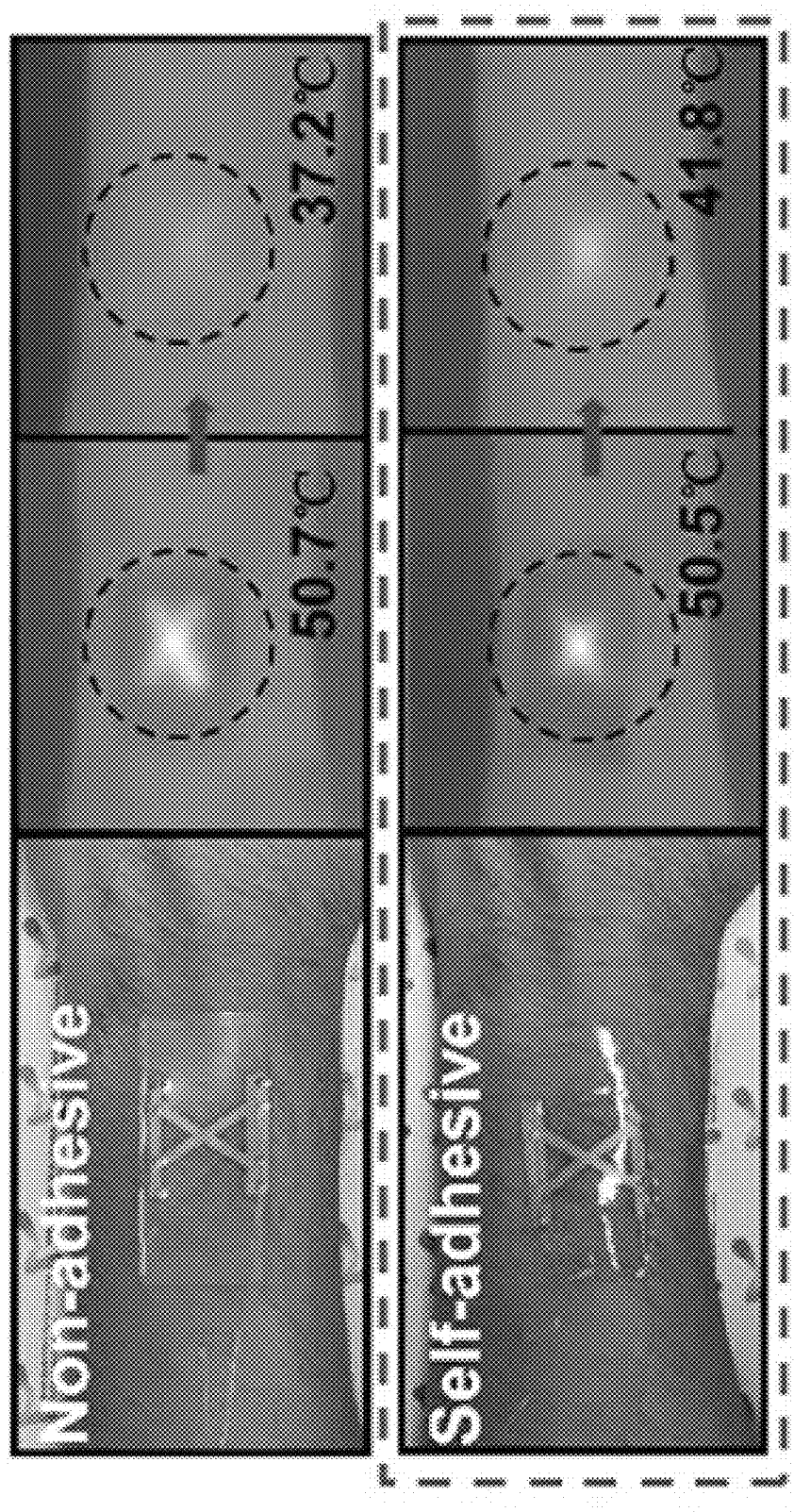

In addition, to compare the heat transfer to the epidermis, a thermal heater patterned in an 'X' shape was attached to the epidermis for 60 seconds. In the case of the non-adhesive thermal heater, the measured epidermal temperature after the detachment of the thermal heater was 37.2° C., and no significant difference in body temperature was observed. Therefore, since the heat transfer from the non-adhesive thermal heater to the epidermis was small, the 'X' shape of the epidermis was not distinguished after the epidermal thermal heater was detached. However, in the case of the attachable epidermal thermal heater, the measured temperature of the epidermis was 41.8° C., and the heat transfer rate was high, and thus the 'X' shape of the epidermis remained relatively well visible even after the heater was detached (see FIG. 12C).

Figure 12D:
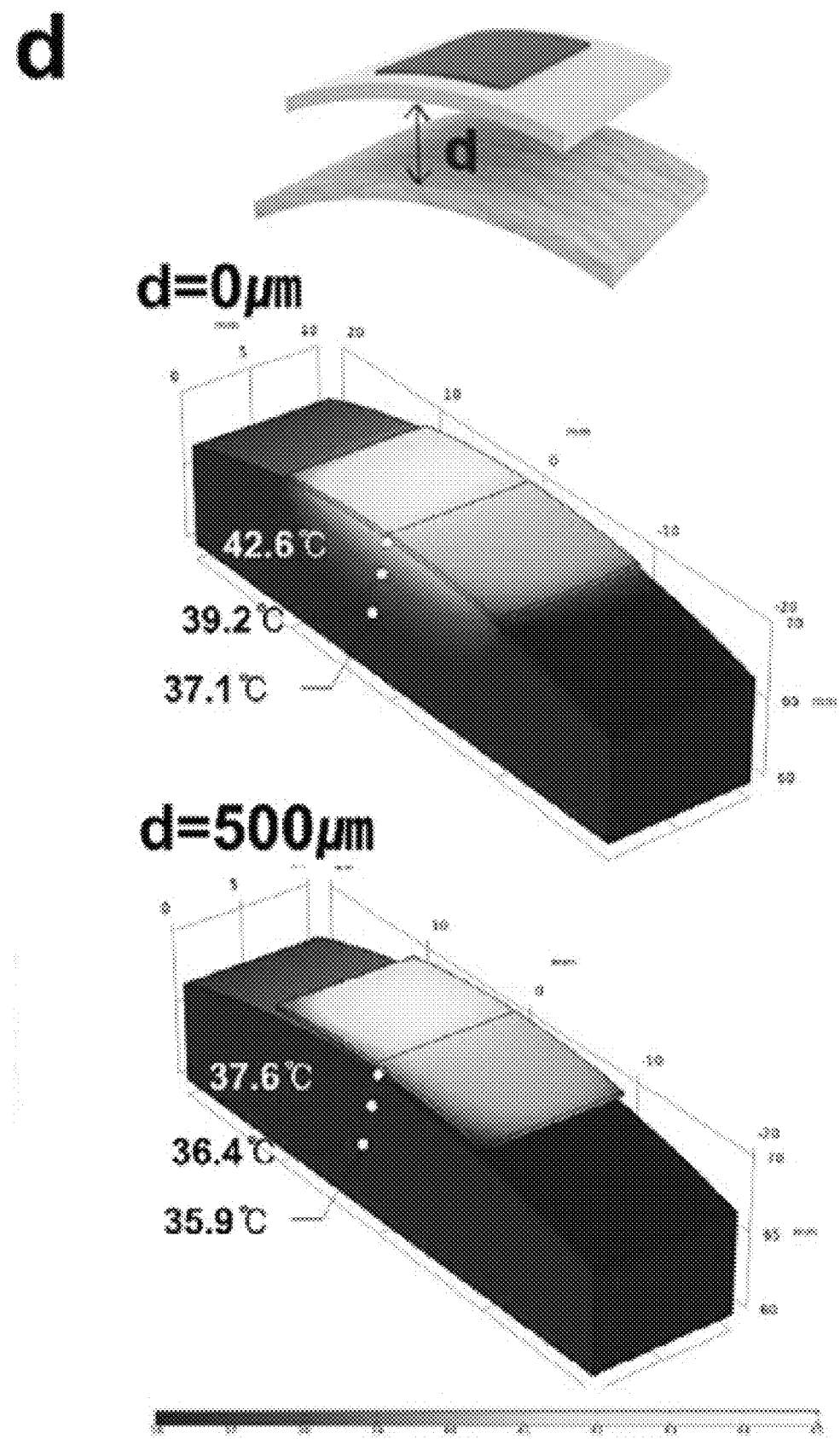

In addition, referring to FIG. 12D, the results described above were confirmed through COMSOL (Computational Simulation). For the heat transfer simulation modeling, the initial temperatures of the thermal heater, human skin, and indoor air were set to 50° C., 36° C., and 25° C., respectively. Considering hairs or dead epidermis of human skin, in the case of a non-adhesive heat heater, almost no heat conduction or heat transfer occurred for 60 seconds in a separated area that was partially separated from human skin by 0.1 to 0.5 mm. On the contrary, in the case of the attachable epidermal thermal heater, the skin temperature reached 42.55° C. in 60 seconds. In addition, the heat generated from the silver nanowires was relatively efficiently transferred to the epidermis because of the conformal contact.

Figure 12E:
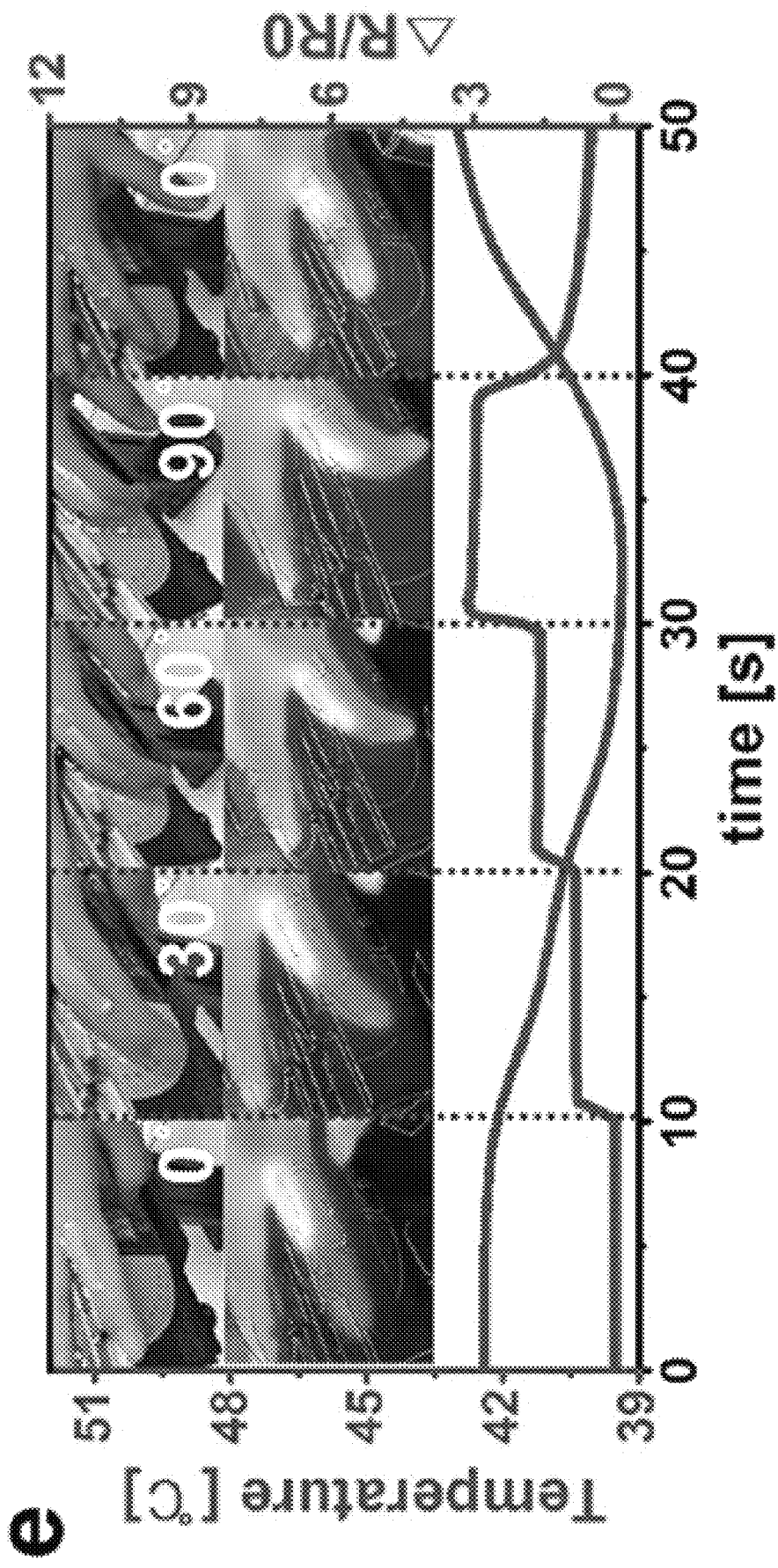

FIG. 12E shows the temperature change of the attachable epidermal heat heater (Fabrication Example 2) according to the motion of the index finger. Referring to FIG. 12E, when the index finger was bent, the temperature dropped from 42.4° C. to 39.4° C., and when the index finger was fully extended, the temperature was recovered to 42.4° C. Due to the high stretchability of the silver nanowires and the photo-polymerized self-adhesive polyurethane substrate (Example 1), the electrical conductivity and the temperature of the attachable epidermal thermal heater were stably recovered while the index finger was moving. In addition, very stable repeatability and stretchability were also observed according to the motion of the attachable epidermal thermal heater. The attachable epidermal thermal heater (Fabrication Example 2) based on the conformal contact with the human epidermis transferred the heat generated from the silver nanowires to the epidermis better than the non-adhesive thermal heater. These results confirmed that the photo-polymerized self-adhesive polyurethane substrate (Example 1), according to the present description, is a biocompatible platform suitable for wearable epidermal devices.

The specific parts of the present description have been described in detail above, and it is clear that these specific technologies are merely preferred embodiments for those skilled in the art, and the scope of the present description is not limited thereto. Therefore, the substantial scope of the present description will be defined by the attached claims and their equivalents.

The present description can be applied to a photo-polymerized polymer curing process and a wearable device manufacturing process, and as research on wearable devices continues, a polyurethane that can be adhered to human skin can be utilized.

What is claimed is:

1. A method of manufacturing a self-adhesive polyurethane using selective photo-polymerization, the method comprising:
    manufacturing a mixed resin by mixing a urethane acrylate oligomer and a photoinitiator;
    depositing the mixed resin to manufacture a polyurethane substrate; and
    manufacturing a self-adhesive polyurethane substrate by performing the selective photo-polymerization of the polyurethane substrate deposited using a laser device,
    wherein the selective photo-polymerization is selectively photo-polymerizing a polyurethane substrate and modifying a crosslinked network of the polyurethane substrate by adjusting a laser scanning speed and a laser scanning spacing distance of the laser device to improve self-adhesiveness and ductility of a photo-polymerized polyurethane substrate.

2. The method of claim 1, wherein the urethane acrylate oligomer is at least one selected from the group consisting of aliphatic urethane diacrylate, aliphatic urethane hexaacrylate, aliphatic urethane triacrylate, aromatic urethane diacrylate, aromatic urethane triacrylate, and aromatic urethane hexaacrylate.

3. The method of claim 1, wherein the photoinitiator is at least one selected from the group consisting of camphorquinone, 2-(dimethylamino methacrylates), phenylbis(2,4,6-trimethylbenzoyl)phosphine oxide, and diphenyl(2,4,6-trimethylbenzoyl)phosphine oxide.

4. The method of claim 1, wherein the laser scanning speed ranges from 250 to 350 mm/s.

5. The method of claim 1, wherein the laser scanning spacing distance ranges from 0.5 to 12 μm.

6. The method of claim 1,
wherein the ductility of the photo-polymerized polyurethane substrate increases as the laser scanning speed increases through a decrease of an area of highly crosslinked network of polyurethane substrate, and
wherein the self-adhesiveness of the photo-polymerized polyurethane substrate increases as the laser scanning spacing distance increases through an expansion of a defective heterogeneous crosslinked network of polyurethane substrate in non-scanned spacing areas.

7. A method of manufacturing attachable epidermal thermal heaters, the method comprising:
coating an organic conductor on a glass substrate;
depositing silver nanowires on the organic conductor;
patterning the silver nanowires deposited; and
attaching a photo-polymerized self-adhesive polyurethane substrate on the silver nanowires patterned,
wherein the photo-polymerized self-adhesive polyurethane substrate is manufactured by:
manufacturing a mixed resin by mixing a urethane acrylate oligomer and a photoinitiator;
depositing the mixed resin to manufacture a polyurethane substrate;
manufacturing a self-adhesive polyurethane substrate by performing a selective photo-polymerization of the polyurethane substrate deposited using a laser device; and
wherein the selective photo-polymerization is selectively photo-polymerizing a polyurethane substrate and modifying a crosslinked network of the polyurethane substrate by adjusting a laser scanning speed and a laser scanning spacing distance of the laser device to improve self-adhesiveness and ductility of a photo-polymerized polyurethane substrate.

8. The method of claim 7,
wherein the ductility of the photo-polymerized polyurethane substrate increases as the laser scanning speed increases through a decrease of an area of highly crosslinked network of polyurethane substrate, and
wherein the self-adhesiveness of the photo-polymerized polyurethane substrate increases as the laser scanning spacing distance increases through an expansion of a defective heterogeneous crosslinked network of polyurethane substrate in non-scanned spacing areas.

9. The method of claim 7, wherein the organic conductor is poly(3,4 ethylenedioxythiophene)-poly(styrenesulfonate) (PEDOT:PSS) or polyaniline (PANI).

10. The method of claim 7, wherein the silver nanowires are patterned by using a UV laser at 10 mW power.

11. The method of claim 7, wherein the photo-polymerized self-adhesive polyurethane substrate has an average thickness ranging from 200 to 400 μm.

12. A method of manufacturing epidermal soft sensors, the method comprising:
manufacturing a mixed resin by mixing a urethane acrylate oligomer and a photoinitiator;
depositing the mixed resin to manufacture a polyurethane substrate;
manufacturing a self-adhesive polyurethane substrate by performing a selective photo-polymerization of the polyurethane substrate deposited using a laser device; and
spraying silver nanowires on the self-adhesive polyurethane substrate to form a nanowire network,
wherein the selective photo-polymerization is selectively photo-polymerizing a polyurethane substrate and modifying a crosslinked network of the polyurethane substrate by adjusting a laser scanning speed and a laser scanning spacing distance of the laser device to improve self-adhesiveness and ductility of a photo-polymerized polyurethane substrate.

13. The method of claim 12,
wherein the ductility of the photo-polymerized polyurethane substrate increases as the laser scanning speed increases through a decrease of an area of highly crosslinked network of polyurethane substrate, and
wherein the self-adhesiveness of the photo-polymerized polyurethane substrate increases as the laser scanning spacing distance increases through an expansion of a defective heterogeneous crosslinked network of polyurethane substrate in non-scanned spacing areas.

* * * * *